(12) United States Patent
Reddi et al.

(10) Patent No.: US 6,355,480 B1
(45) Date of Patent: Mar. 12, 2002

(54) METHODS AND COMPOSITIONS FOR MODULATING SPERMATOGENESIS

(75) Inventors: Prabhakara P. Reddi; Charles J. Flickinger; John C. Herr, all of Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 09/340,323

(22) Filed: Jun. 25, 1999

Related U.S. Application Data

(60) Provisional application No. 60/090,942, filed on Jun. 26, 1998, and provisional application No. 60/122,142, filed on Feb. 26, 1999.

(51) Int. Cl.$^7$ ......................... C07H 21/04; C12N 15/63; C12N 5/00
(52) U.S. Cl. ......................... 435/325; 435/320.1; 800/8; 800/18; 536/24.1; 536/23.1; 536/23.5
(58) Field of Search .............................. 536/23.1, 23.5, 536/24.1; 435/320.1, 325; 800/8, 18

(56) References Cited

U.S. PATENT DOCUMENTS

| | | | |
|---|---|---|---|
| 5,266,488 A | 11/1993 | Ordahl et al. | 435/240.2 |
| 5,374,544 A | 12/1994 | Schwartz et al. | 435/172.3 |
| 5,502,176 A | 3/1996 | Tenen et al. | 536/24.1 |
| 5,643,746 A | 7/1997 | Polakowska et al. | 435/69.1 |
| 5,698,389 A | 12/1997 | de la Brousse et al. | 435/4 |

FOREIGN PATENT DOCUMENTS

| | | |
|---|---|---|
| EP | 0 582 796 A1 | 2/1994 |
| WO | WO 97/17359 | 5/1997 |

OTHER PUBLICATIONS

Hillier et al. EST Database Accession No H93373, Dec. 1, 1995.*
Cameron ER. Molecular Biotechnology 7:253–265, 1997.*
Ausubel FM et al., 1989, *Current Protocols in Molecular Biology*, vol. 1, Green Publishing Associates, Inc., and John Wiley & Sons, Inc. New York. p. 2.10.3.
Bartell JG et al., "Expression of the rat testis–specific histone H1t gene in transgenic mice. One kilobase of 5′–flanking sequence mediates correct expression of a lacZ fusion gene", J Biol Chem. Feb. 1996 23;271(8):4046–54.
Beaton S et al., "Cloning and partial characterization of the cDNA encoding the fox sperm protein FSA–Acr.1 with similarities to the SP–10 antigen", Mol Reprod Dev. Feb. 1995;40(2):242–52.
Beecher KL et al., "Evidence that 68–kilodalton and 54–51–kilodalton polypeptides are components of the human sperm fibrous sheath", Biol Reprod. Jan 1993;48(1):154–64.
Bellve AR et al., "Spermatogenic cells of the prepuberal mouse. Isolation and morphological characterization", J Cell Biol. Jul. 1977;74(1):68–85.
Cooker LA et al., "Genomic structure and promoter activity of the human testis lactate dehydrogenase gene", Biol Reprod. Jun. 1993;48(6):1309–19.
Coonrod SA et al., "Inhibition of bovine fertilization in vitro by antibodies to SP–10", J Reprod Fertil. Jul. 1996;107(2):287–97.
Cormack BP et al., "FACS–optimized mutants of the green fluorescent protein (GFP)", Gene. 1996;173(1 Spec No):33–8.
Foster JA et al., "Human SP–10: acrosomal distribution, processing, and fate after the acrosome reaction", Biol Reprod. Dec. 1994;51(6):1222–31.
Freemerman AJ et al., "Tissue specificity of the acrosomal protein SP–10: a contraceptive vaccine candidate molecule", Biol Reprod. Mar. 1994;50(3):615–21.
Freemerman AJ et al., "Cloning and sequencing of baboon and cynomolgus monkey intra–acrosomal protein SP–10: hormology with human SP–10 and a mouse sperm antigen (MSA–63)", Mol Reprod Dev. Feb. 1993;34(2):140–8.
Galcheva–Gargova Z et al., "The rat proenkephalin germ line promoter contains multiple binding sites for spermatogenic cell nuclear proteins", Mol Endocrinol. Aug. 1993;7(8):979–91.
Haas J et al., "Codon usage limitation in the expression of HIV–1 envelope glycoprotein", Curr Biol. Mar. 1, 1996;6(3):315–24.
Herr JC et al., "Identification of human acrosomal antigen SP–10 in primates and pigs", Biol Reprod. Feb. 1990;42(2):377–82.
Howard T et al., "Sperm–specific expression of angiotensin–converting enzyme (ACE) is mediated by a 91–base–pair promoter containing a CRE–like element", Mol Cell Biol. Jan. 1993;13(1):18–27.
Iannello RC et al, "Regulation of Pdha–2 expression is mediated by proximal promoter sequences and CpG methylation", Mol Cell Biol. Feb. 1997;17(2):612–9.
Ito E et al., "Erythroid transcription factor GATA–1 is abundantly transcribed in mouse testis", Nature. Apr. 1, 1993;362(6419):466–8.

(List continued on next page.)

*Primary Examiner*—Dave T. Nguyen
*Assistant Examiner*—Bam R. Shukla
(74) *Attorney, Agent, or Firm*—Pennie & Edmonds LLP

(57) ABSTRACT

The present invention relates to compositions and methods for screening compounds that modulate meiotic progression. In particular, it relates to compositions comprising nucleotides from the mouse 5′ regulatory region, and transcriptionally active fragments thereof, that control the expression of a testis-enriched protein, SP-10. Specifically provided are expression vectors, host cells, and transgenic animals. The SP-10 promoter controls the expression of a heterologous gene, e.g., green fluorescent protein. The invention relates to methods for using the vectors, cells, and animals for screening candidate molecules for agonists and antagonists of sperm development and fertilization. Methods for using molecules and compounds identified by the screening assays for therapeutic treatments are provided.

6 Claims, 14 Drawing Sheets

OTHER PUBLICATIONS

Figure 1:
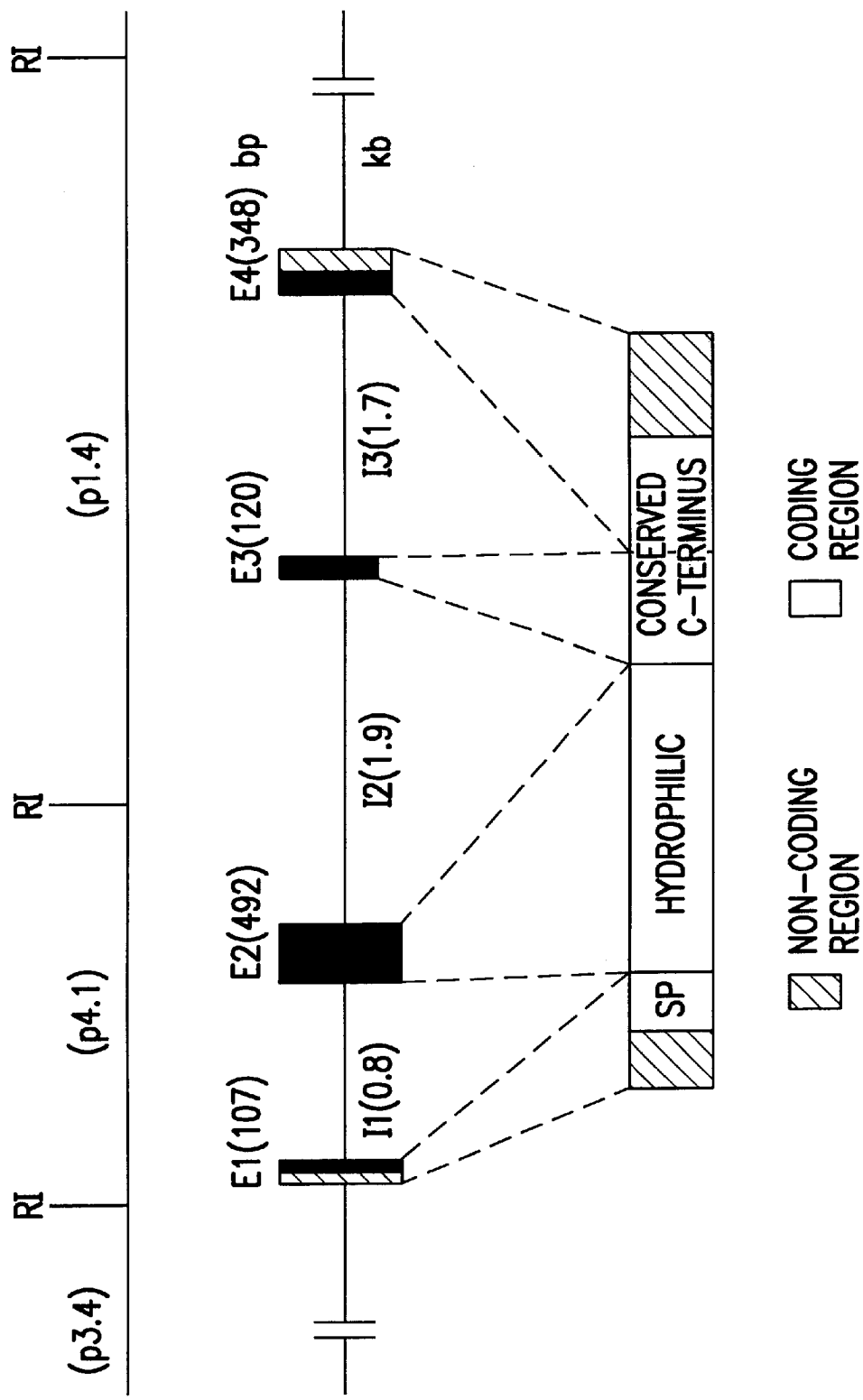

Kageyama R et al., "Nuclear factor ETF specifically stimulates transcription from promoters without a TATA box", J Biol Chem. Sep. 15, 1989;264(26):15508–14.

Kallio M et al., "Immunolocalization of alpha–tubulin, gamma–tubulin, and CENP–E in male rat and male mouse meiotic divisions: pathway of meiosis I spindle formation in mammalian spermatocytes", Dev Biol. Mar. 1, 1998;195(1):29–37.

Kramer A., "The structure and function of proteins involved in mammalian pre–mRNA splicing", Annu Rev Biochem. 1996;65:367–409.

Kurth BE et al., "Stage–specific detection of mRNA for the sperm antigen SP–10 in human testes", Anat Rec. Aug. 1993;236(4):619–25.

Kurth BE et al., "Localization of sperm antigen SP–10 during the six stages of the cycle of the seminiferous epithelium in man", Biol Reprod. May 1991;44(5):814–21.

Langford KG et al., "Transgenic mice demonstrate a testis–specific promoter for angiotensin–converting enzyme", J Biol Chem. Aug. 25, 1991;266(24):15559–62.

Li S et al., "Transgenic mice demonstrate a testis–specific promoter for lactate dehydrogenase, LDHC", J Biol Chem. Nov. 20, 1998;273(47):31191–4.

Liang L et al., "FIGalpha, a germ cell specific transcription factor involved in the coordinate expression of the zona pellucida genes", Development. Dec. 1997;124(24):4939–47.

Liu F et al., "Novel repeat elements direct rat proenkephalin transcription during spermatogenesis", J Biol Chem. Feb. 21, 1997;272(8):5056–62.

Liu MS et al., "Molecular and developmental studies of a sperm acrosome antigen recognized by HS–63 monoclonal antibody", Biol Reprod. May 1992;46(5):937–48.

Nantel F et al., "Spermiogenesis deficiency and germ–cell apoptosis in CREM–mutant mice", Nature, Mar. 14, 1996;380(6570):159–62.

Nayemia K et al., "Functional and molecular characterization of the transcriptional regulatory region of the proacrosin gene", J Biol Chem. Dec. 23, 1994;269(51):32181–6.

Okabe M et al., "Green mice as a source of ubiquitous green cells", FEBS Lett. May 5, 1997;407(3):313–9.

Olson GE et al., "An antigenically related polypeptide family is a major structural constituent of a stable acrosomal matrix assembly in bovine spermatozoa", Biol Reprod. Aug. 1997;57(2):325–34.

Parvinen et al., "Transillumination–phase–contrast microscopic techniques for evaluation of male germ cell toxicity and mutagenicity", in *Methods in Toxicology*, vol. 3, Chapin and Heindel (eds.), part A, 142, Academic Press, New York, 1993.

Parvinen M and Hecht NB, "Identification of living spermatogenic cells of the mouse by transillumination–phase contrast microscopic technique for 'in situ' analyses of DNA polymerase activities", Histochemistry. 1981;71(4):567–79.

Parvinen M and Ruokonen A, "Endogenous steroids in the rat seminiferous tubules. Comparisons of the stages of the epithelial cycle isolated by transillumination–assisted microdissection", 1982, J Androl 3:211–220.

Parvinen M et al., "Identification and enzyme quantitation of the stages of the seminiferous epithelial wave in the rat", Anat Rec. Dec. 1972;174(4):435–49.

Penttila TL et al., "Haploid gene expression: temporal onset and storage patterns of 13 novel transcripts during rat and mouse spermiogenesis", Biol Reprod. Sep. 1995;53(3):499–510.

Penttila TL et al., "Follicle–stimulating hormone regulates the expression of cyclic protein–2/cathepsin L messenger ribonucleic acid in rat Sertoli cells in a stage–specific manner", Mol Cell Endocrinol. Sep. 22, 1995;113(2):175–81.

Peschon JJ et al., "Spermatid–specific expression of protamine 1 in transgenic mice", Proc Natl Acad Sci U S A. Aug. 1987;84(15):5316–9.

Prasher DC et al., "Primary structure of the Aequorea victoria green–fluorescent protein", Gene, Feb. 15, 1992;111(2):229–33.

Reddi PP et al., "Round spermatid–specific transcription of the mouse SP–10 gene is mediated by a 294–base pair proximal promoter", Biol Reprod. Nov. 1999;61(5):1256–66.

Reddi et al., "Minimal promoter essential for round spermatid–specific gene expression resides within the—420 to +28 BP region of the SP–10 gene", Biology of Reproduction. Aug. 1998;58(1):163.

Reddi PP et al., "Complementary deoxyribonucleic acid cloning and characterization of mSP–10: the mouse homologue of human acrosomal protein SP–10", Biol Reprod. Oct. 1995;53(4):873–81.

Robinson MO et al., "Transcriptional regulatory regions of testis–specific PGK2 defined in transgenic mice", Proc Natl Acad Sci U S A. Nov. 1989;86(21):8437–41.

Sjoblom T et al., "Expression of p53 in normal and gamma–irradiated rat testis suggests a role for p53 in meiotic recombination and repair", Oncogene. Jun. 20, 1996;;12(12):2499–505.

Smale ST et al., "The 'initiator' as a transcription control element", Cell, Apr. 7, 1989;57(1):103–13.

Stewart TA et al., "Heploid–specific transcription of protamine–myc and protamine–T–antigen fusion genes in transgenic mice", Mol Cell Biol. Apr. 1988;8(4):1748–55.

Stoler MH., "In sity hybridization", Clin Lab Med. Mar. 1990;10(1):215–36.

Van Dissel–Emiliani et al., "Inhibin reduces spermatogonial numbers in testes of adult mice and Chinese hamsters", Endocrinology, Oct. 1989; 125(4):1899–903.

vanWert JM et al., "The TE promoter element of the histone H1t gene is essential for transcription in transgenic mouse primary spermatocytes", Biol Reprod. Sep. 1998;59(3):704–10.

Wolkowicz MJ et al., "Refinement of the differentiated phenotype of the spermatogenic cell line GC–2spd", Biol Reprod. Oct. 1996;55(4):923–32.

Wright RM et al., "Cloning and characterization of the gene coding for the human acrosomal protein SP–10", Biol Reprod. Aug. 1993;49(2):316–25.

Wright RM et al., "Cloning and sequencing of cDNAs coding for the human intra–acrosomal antigen SP–10", Biol Reprod. Apr. 1990;42(4):693–701.

Yan W et al., "Stage–specific expression and phosphorylation of retinoblastoma protein (pRb) in the rat seminiferous epithelium", Mol Cell Endocrinol. Sep. 19, 1997;132(1–2):137–48.

Zambrowicz BP et al., "Analysis of the mouse protamine 1 promoter in transgenic mice", Proc Natl Acad Sci U S A. Jun. 1, 1993;90(11):5071–5.

Zenzie–Gregory B et al., "Mechanism of initiator–mediated transcription: evidence for a functional interaction between the TATA–binding protein and DNA in the absence of a specific recognition sequence", Mol Cell Biol. Jul. 1993;13(7):3841–9.

www.ncbi.nlm.nih.gov (National Center for Biotechnology Information) Genbank Accession No. S65606ls1. Sp–10= intra–acrosomal protein {alternatively spliced} [human, liver, Genomic, 916 nt, segment 1 of 4]. Database [Online]. Last update: Nov. 11, 1993. Accessed on: Feb. 14, 2000.

www.ncbi.nlm.nih.gov (National Center for Biotechnology Information) Genbank Accession No. U31992. Mus musculus acrosomal protein MSP–10 (acrv1) mRNA, complete cds. Database [Online]. Last update: Mar. 8, 1996. Accessed on: Feb. 14, 2000.

www.ncbi.nlm.nih.gov (National Center for Biotechnology Information) Genbank Accession No. U55761. Cloning vector pEGFP–1, complete sequence, enhanced green fluorescent protein (egfp) and neomycin phosphotransferase genes, complete cds. Database [Online]. Last update: Jun. 15, 1996. Accessed on: Feb. 14, 2000.

* cited by examiner (−420 bp)

```
  1  cctccaatct taggactaac ctcagtttga agccaaaacc actcagctaa
 51  tctcagcaaa gattagtctt ccagagtgca aaccagagcc atgaaacact
101  cagtcaaaca gaaagtaacc aggtcaccac acttcactgt tgaccctctg
151  caaagaagtg ctatcttta aactttcact aaaagaacat gtgtgattct
201  ggtaacattt tttgtttgtt tttgaagcta ccccta‌acac actattctac
251  acacagaaaa tgctcttcac tagtggcatt gcatgggttg cagggccagc
301  ctgcctgaac aggatgtaag aggaacaacc cattgtgagg acacatagat
351  tgtttctcaa gttctagaat tcccagaggc tctgattcaa cactgggagc
401  gtttgctcag tttcttctca gctcttgagt gtgcca
```

(+28 bp)

FIG.3

```
                       CAT box
m   -408------gcctccaatctta-ggactaacctcagtttgaagccaaaaccactcagc   -361
              |||||||||:|:  |   ||||: |:|:|||||||||| ||| :||||
h   -459------ccctccaatcctgtata--aaccc-aatctgaagccaaatccagccagc   -413 m   ----------taatctcagcaaagattagtcttccagagtgcaaaccagagccatgaaa   -311
              |||   |||:||:|:|:|::|||||||:||:|| :|:|||||||| ||||
h   attcaggtgataaagtcaacagaggtcaaccttccagggtacagatcagagccaagaaa   -354
                                                       Hin cII
m   cactcagtc--------aaacagaaagtaaccaggtcaccacacttcactgtt---gac   -264
    :|| | |:         |||||||||::||:|   |::|||::|||:|||:    :||
h   ggctgatttagaaagccaaacagaaaacaatc-aacaattacatctcattgtcaaaaac   -296
                         GATA-1                       E-box*
m   -cctctgcaaaga-agtgc-tatcttttaaactttcactaaaagaacatgtgtgttctg   -208
     |:|:|  ||||| |||   ||||||||||||||| :  |||:||:|||||: ||:||
h   acttta-aaagacagtagatatctttaaactttattacaaaaatatgtgcttttg      -239
        HNF-5*                    ETF
m   gtaacattttttgtttgtttttt---------gaagctaccccctaacacactattctaca  -158
    ||||:|:||||| ||| |||||          | || || |||:|||||||:::||:||
h   gtaatacttttttttttttttttaaagataggggcagatagccccaacacactaccctgca  -180
                            P3
m   cacagaaaat-------gctcttcactagtggcat-tgc-atgggttgc--agggccag   -110
    ||||||||||       | ||||||||||||:  || ||  |||||||| ||||||||:
h   cacagaaaataatcattggtcttcactagtgaaataagcagtgggttgctaagggccaa   -121
       P2     Ets-1                                   CRE-like
m   cctgcctgaacaggatgtaagag-------gaa--caacccattgtgaggacacataga   -60
    |:|||||||||||| |:: :||         ||: |||||||||||:|| ||||:|:
h   cttgcctgaacaggctacacaagaacctcagagcccaacccattgtgaagaaacatggg   -62
          P1                                      AP1*
m   ttgtttctcaagttctagaattcccagaggctctgattcaacactgggagcgtttgc-- -3
    ||::|||| |:||||||||||||||||:||||||| |||||:||||||:||| |||||
h   ttacttctgaggttctagaattcccagaagctctgcttcagcactggaagcttttgctc -3
    +1 Inr
m   tcagttt-cttctcagctct-tgag-----tgtg--ccacattagagatctttatttac  +48
       |||||| |||| ||||||| |||      ||||  |||||:|:|: :|:::| ||| |
h   gcagtttgcttcatagctctgtgaagaagctgtggcccacactggggtcccctctttc  +57 m   ctaaatcaaa atg aag gag tta atc tta ctg ggt ctt tat ctg        +91
    |||||||| |:
h   ctaaatccag atg aac agg ttt ctc ttg cta atg agt ctt tat        +100
```

FIG.4

METHODS AND COMPOSITIONS FOR MODULATING SPERMATOGENESIS

This application claims priority under 35 U.S.C. §119 (e) to U.S. provisional patent application no. 60/090,942 filed Jun. 26, 1998, and U.S. provisional patent application No. 60/122,142 filed Feb. 26, 1999, the entire contents of which are incorporated herein by reference in their entirety. This invention was made with government support under grant number HD29099, awarded by the National Institutes of Health a grant from the Andrew W. Mellon Foundation and a grant from the Fogarty International Center at NIH. The government has certain rights in the invention.

1. INTRODUCTION

The present invention relates to compositions and methods for screening compounds that modulate meiotic progression and spermatogenesis. In particular, it relates to compositions comprising nucleotides from the mouse 5' regulatory region, and transcriptionally active fragments thereof, that control the expression of a testis-enriched protein, SP-10. Specifically provided are expression vectors, host cells, and transgenic animals, wherein the SP-10 promoter controls the expression of a heterologous gene, e.g., green fluorescent protein. The invention relates to methods for using said vectors, cells, and animals for screening candidate molecules for agonists and antagonists of sperm development and fertilization. Methods for using molecules and compounds identified by the screening assays for therapeutic treatments are provided.

2. BACKGROUND OF THE INVENTION

Meiotic arrest in spermatogenesis is a well-documented cause of infertility in men. The early stages of spermatogenesis are key steps in the terminal differentiation of male germ cells. Therefore, proteins expressed in early spermatogenesis are likely to be important targets for agonists and antagonists of fertilization. To date, no transcriptional regulatory elements or trans-acting factors involved in the early round spermatid gene expression have been identified. One problem has been the absence of an in vitro model system that recapitulates spermatogenesis. Such a model for terminal differentiation of male germ cells could be used to identify and characterize transcriptional regulators of spermiogenesis. Such regulators could then be targeted to screen for novel compounds and drugs that can be used as treatments for infertility and as contraceptives.

Spermatogenesis is a complex and continuous process of germ cell differentiation which consists of three phases: a proliferative phase, involving the spermatogonial stem cells; a meiotic phase, in which the spermatocytes undergo reduction divisions; and spermiogenesis during which the haploid spermatids undergo extensive biochemical and morphological changes to become spermatozoa. This progression of undifferentiated spermatogonia into spermatozoa is dependent upon precise, developmental stage-specific and germ cell type-specific gene expression.

The 5' flanking sequences for a limited number of testis-specific genes have been cloned, and the minimal promoters required for testis-specific gene expression have been defined in transgenic mice. These include phosphoglycerate kinase (Pgk-2), proenkephalin, acrosin, histone Hit, private dehydrogenase (Pdha-2), and lactate dehydrogenase (Ldhc-4) genes (Robinson et al., 1989, Proc. Natl. Acad. Sci. U.S.A. 86:8437–8441; Galcheva-Gargova, 1993, Mol. Endocrinol., 7:979–991; Nayernia et al., 1994, J. Biol. Chem. 51:32181–32186; Bartell et al., 1996, J. Biol. Chem. 271:4046–4054; Iannello et al., 1997, Mol. Cell. Biol. 17:612–619; Li et al., 1998, J. Biol. Chem. 273:31191–31194) which are expressed in the spermatocytes during meiotic phase, and protamine 1, protamine 2, and testis angiotensin converting enzyme (t-ACE) genes (Peschon et al., 1987, Proc. Natl. Acad. Sci. USA. 84:5316–5319; Stewart et al., 1988, Mol. Cell. Biol. 8:1748–1755; Langford et al., 1991, J. Biol. Chem. 266:15559–15562) which are expressed in the late spermatids.

Promoter analysis of genes uniquely expressed in early round spermatids, however, has not been previously reported. SP-10 is an intra-acrosomal protein first identified in human sperm (Herr, 1990, Biol. Reprod. 42:377–382) and subsequently shown to be present in the acrosome of monkey, baboon (Freemerman et al., 1993, Mol. Repr. Dev. 34:140–148), fox (Beaton et al., 1995, Mol. Repr. Dev. 40:242–252.), mouse (Reddi et al., 1995, Biol. Reprod. 53:873–881), and bull (Olson et al., 1997, Biol. Reprod. 57:325–30 334) sperm. Following the acrosome reaction, some amount of SP-10 protein is retained on the inner acrosomal membrane (Foster et al., 1994, Biol. Reprod. 51:1222–1231).

The finding that anti-SP-10 antibodies block sperm-egg interactions in vitro (Coonrod et al., 1996, J. Reprod. Fert. 107:287–297) suggested a role for SP-10 during fertilization. In the human seminiferous epithelium, SP-10 mRNA was first detected in early Golgi phase step 1 spermatids during formation of the acrosomal granule (Kurth et al., 1993, Anat. Rec. 236:619–625). An extensive tissue specificity analysis indicated that SP-10 transcription is testis-specific (Freemerman et al., 1994, Biol. Reprod. 50:615–621).

The invention disclosed herein, based on the identification of SP-10 gene sequences, provides a useful model for the characterization and modulation of testis-specific gene transcription during acrosome biogenesis in round spermatids.

Citation of references hereinabove shall not be construed as an admission that such references are prior art to the present invention.

3. SUMMARY OF THE INVENTION

The invention disclosed herein provides a model for testis-specific gene transcription during round spermatid development. The invention is based in part on the functional characterization described herein of the novel SP-10 promoter, the first testis-specific gene promoter found to be active in early round spermatids.

The present invention provides compositions and methods for screening compounds that modulate meiotic progression and spermatogenesis. In particular, it provides compositions comprising nucleotides from the mouse SP-10 5' regulatory region, and transcriptionally active fragments thereof, as well as nucleic acids that hybridize under highly stringent conditions to such nucleotides, that control the expression of a testis-enriched protein, SP-10. Specifically provided are expression vectors comprising the SP-10 5' regulatory region, and transcriptionally active fragments thereof, operably associated to a heterologous reporter gene, e.g., green fluorescent protein (GFP), and host cells and transgenic animals containing such vectors. The invention also provides to methods for using such vectors, cells, and animals for screening candidate molecules for agonists and antagonists of sperm development, which will in turn act as modulators of fertility. Methods for using molecules and compounds identified by the screening assays for therapeutic treatments are provided.

For example, and not by way of limitation, a composition comprising a reporter gene is operatively linked to an SP-10 gene regulatory sequence, herein called the SP-10 promoter. The SP-10 driven reporter gene is expressed as a transgene in mice. The transgenic mice, and cells derived from the testes of such transgenic mice, can be used to screen compounds for candidates useful for modulating development of the haploid round spermatid. Without being bound by any particular theory, such molecules are likely to interfere with the function of trans-acting factors, such as transcription factors as well as cis-acting elements, such as promoters and enhancers required for early spermatogenesis. As such, they are potentially powerful candidates for fertility treatment and for use as contraceptives.

In one embodiment, the invention provides methods for high throughput screening of compounds that modulate sperm differentiation. In this aspect of the invention, testicular cells are removed from the transgenic mice and cultured in vitro. The expression of the reporter gene is used to monitor testes-specific gene activity. In a specific embodiment, green fluorescent protein (GFP) is the reporter gene. Compounds identified by this method can be tested further for their effect on fertilization in normal mice.

In another embodiment, the transgenic mouse model of the invention can be used for in vivo screening to test the mechanism of action of candidate fertility drugs and contraceptive agents and their effect on spermatogenesis. Specifically, the effects of contraceptive agents on terminal differentiation of spermatids into sperm, i.e., spermiogenesis, can be assayed.

In another embodiment the invention provides therapies for targeting defects in meiotic progression leading to azospermia and infertility. Compounds that interfere with acrosomal biogenesis, which marks the beginning of the terminal phase of male germ cell differentiation, can provide therapies for targeting defects in spermatogenesis leading to azospermia and infertility.

In another embodiment, spermatogenic cells derived from transgenic mice are used as a source for transplantation experiments. In various embodiments, transplanted spermatogenic cell SP-10-driven reporter genes are used as markers in assays to test the effect of conditions and factors on various stages of spermiogenesis.

In another embodiment, a gene therapy method for contraception is provided. SP-10 promoter sequences are used to drive spermatid-specific expression of drugs or toxins and introduced in the testis. The method comprises introducing an SP-10 regulatory sequence operatively associated with a drug or toxin gene into testicular cells. In a specific embodiment, the invention provides a gene therapy method for treatment of cancer or other proliferative disorder. The SP-10 promoter is used to direct the expression of one or more proteins specifically in testicular tumor cells of a patient.

The invention further provides methods for screening for novel transcription factors that modulate the SP-10 promoter. Such novel transcription factors identified by this method can be used as targets for male contraceptive discovery.

4. BRIEF DESCRIPTION OF THE FIGURES

FIG. 1. Genomic organization of the mSP-10 gene. The top panel shows the insert of the mSP-10 genomic phage clone, as well as the subclones (p 3.4, p 4.1, p1.4) generated using the EcoRI (RI) sites. The middle panel shows the genomic structure. The four exons, E1, E2, E3, and E4 are represented by filled boxes, and the untranslated portions of E1 and E4 are marked by patterned boxes. The sizes of exons and introns are indicated in parenthesis, with intron sizes estimated by gel electrophoresis. The bottom panel is a schematic representation of the cDNA depicting the domains of the mSP-10 protein encoded by the exons. The coding and non-coding parts of the mSP-10 cDNA are also indicated. Abbreviations: bp, basepair; kb, kilobase; SP, signal peptide.

Figure 2:
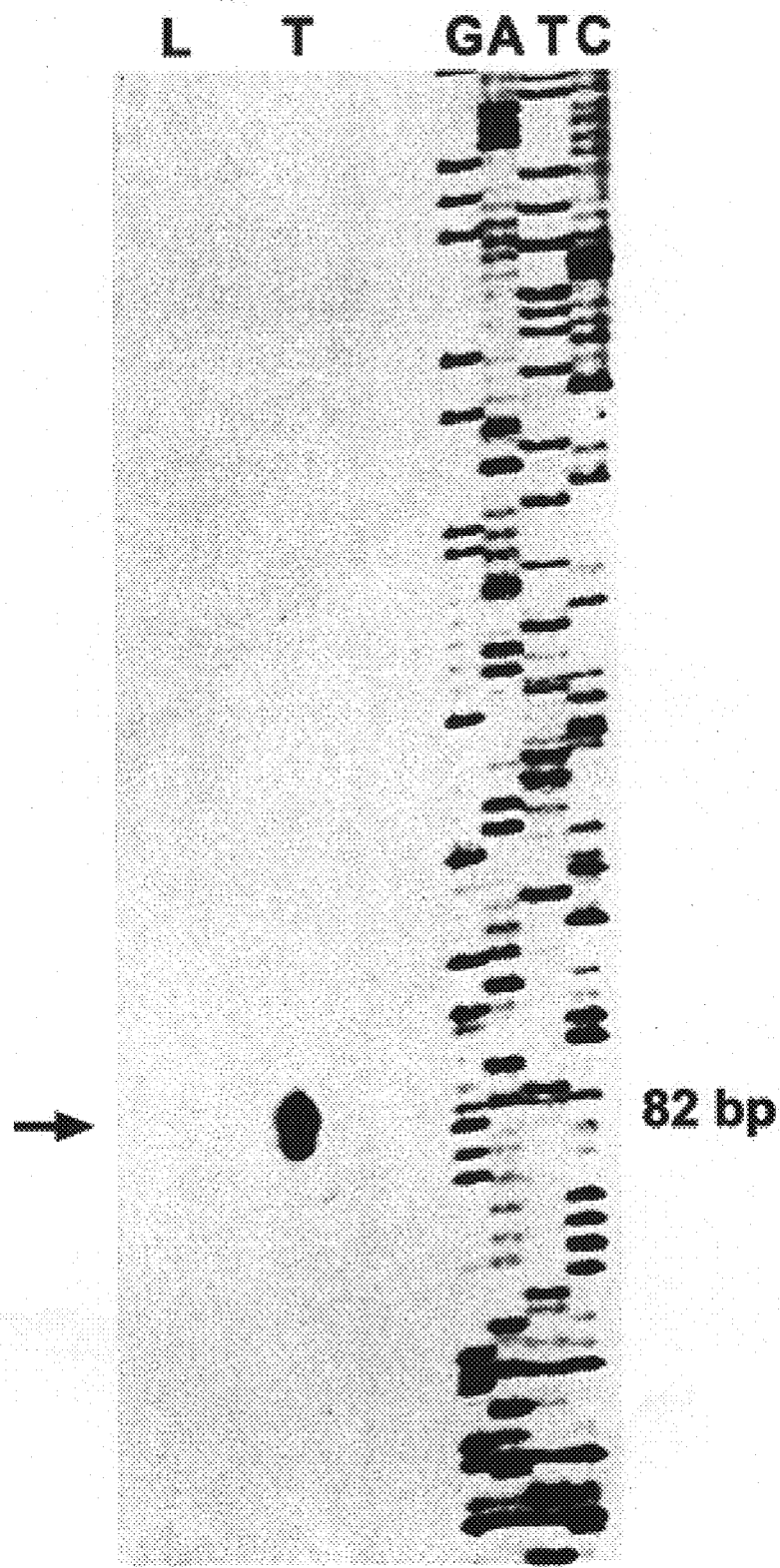

FIG. 2. Determination of the transcriptional start site of mSP-10 by primer extension method. A synthetic oligonucleotide primer (29 bases) labeled with $\gamma^{32}P$ ATP was hybridized to mRNA of mouse testis (T) and liver (L), and the cDNA was synthesized using avian myeloblastosis virus reverse transcriptase. The extension products were analyzed by electrophoresis on a 6% denaturing sequencing gel. The major extension product, 82bp in length, is shown with an arrow. The four lanes to the right designated G,A,T,C contain the M13mp18 sequencing ladder used for size estimation.

FIG. 3. Polynucleotide sequences comprising the regulatory region, and transcriptionally active elements thereof, of the mouse SP-10 gene (SEQ ID NO:1).

FIG. 4. Structure of the SP-10 promoter. Comparison of the novel mSP-10 promoter (m) (SEQ ID NO:2) of the present invention characterized in this study with the corresponding region of the human (h) SP-10 gene (SEQ ID NO:3) described previously (Kramer et al., 1996, Annu. Rev. Biochem. 65, 367–409). Identical bases are indicated by a "|" symbol, whereas A to G (purine) and T to C (pyrimidine) substitutions indicated by a ":" symbol were considered similarities. The +1 indicates the transcription start site. Conserved cis-acting elements which constituted recognition sequences for known transcription factors are indicated by the highlighted regions. The three conserved palindrome sequences are designated P1, P2, and P3. An asterisk indicates those cis-acting elements present in the mouse gene alone. Codons for the first eleven amino acids of the mouse and human SP 10 proteins are depicted as triplets, in italicized letters. The dashed underline denotes the primer used in the primer extension experiment. The −408 to +58 bp 5' flanking region of mSP-10 shares 80% similarity with the −459 to +67 bp region of the human SP-10 gene. The Hinc II restriction site used for subcloning is indicated in italics at the −266 bp position in the mSP-10 sequence. Abbreviations: m, mouse; h, human.

FIG. 5. Determination of a promoter fragment sufficient for testis-specific transcription of the mSP-10 gene (SEQ ID NO:1). A. schematic representation of putative regulatory elements in the −408 to +28 bp mSP-10 promoter fragment. B. map of promoter deletion constructs fused to the GFP reporter gene and the promoter activity of each construct in the testis of transgenic mice. The numbers indicate nucleotide positions of the 5' flanking region of mSP-10, and the transcription start site is considered as +1. Decapsulated testis (phase) was placed in a glass dish and viewed using epifluorescence microscope through an FITC filter set (fluorescence). C. Testis-specific expression of GFP mRNA in transgenic mice. RT-PCR analysis of mRNA isolated from brain (B), liver (L), kidney (K), heart (H), prostate (P), and testis (T) of transgenic mice using either GFP- (gfp) or beta actin-specific (f3-actin) primers. The −408SP10-gfp, and −266SP10-gfp mice expressed GFP mRNA in the testis, but not in the somatic tissues. The −91SP10-gfp mice failed to express GFP in any tissue.

Figure 6A:
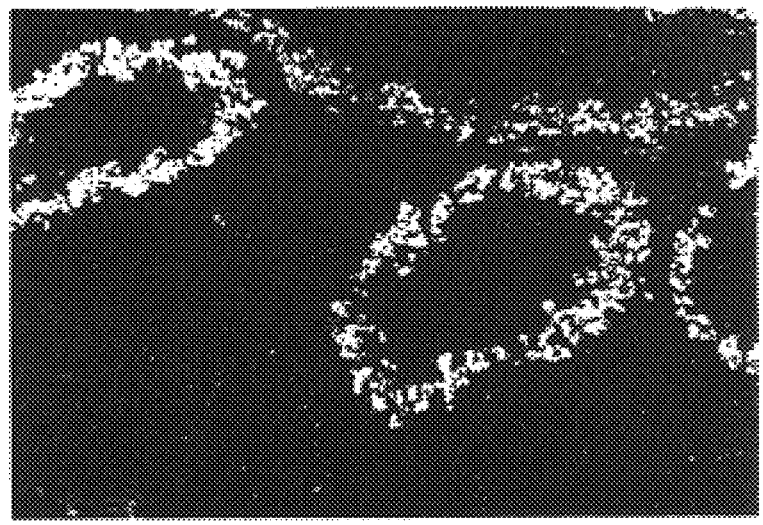
Figure 6B:
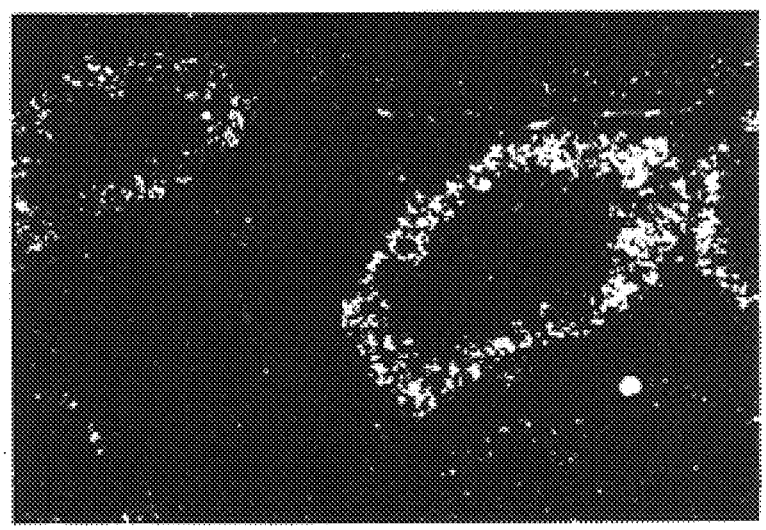
Figure 6C:
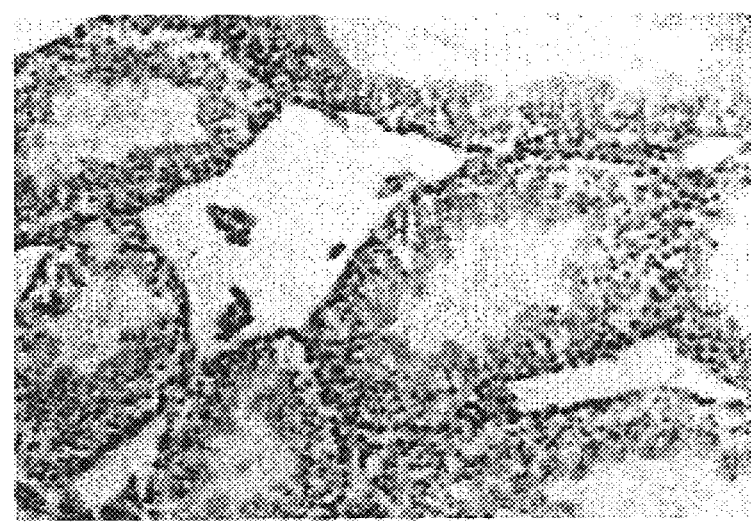

FIG. 6. Reporter gene expression mimics the spatial and temporal pattern of the endogenotis mSP-10 gene expression: In situ hybridization was performed on serial cross sections of the testis of a −408SP10-gfp transgenic line. Panels A and B represent dark field images of sections probed with $^3$H-labeled SP-10 and GFP antisense riboprobes respectively. Panel C shows bright field image after H&E staining. Note that identical tubules in panels A and B showed endogenous SP-10 and GFP transgene hybridization signals, respectively, which indicates that the −408 to +28 bp SP-10 promoter fragment accurately mimicked the endogenous mSP-10 promoter activity in transgenic mice.

Figure 7:
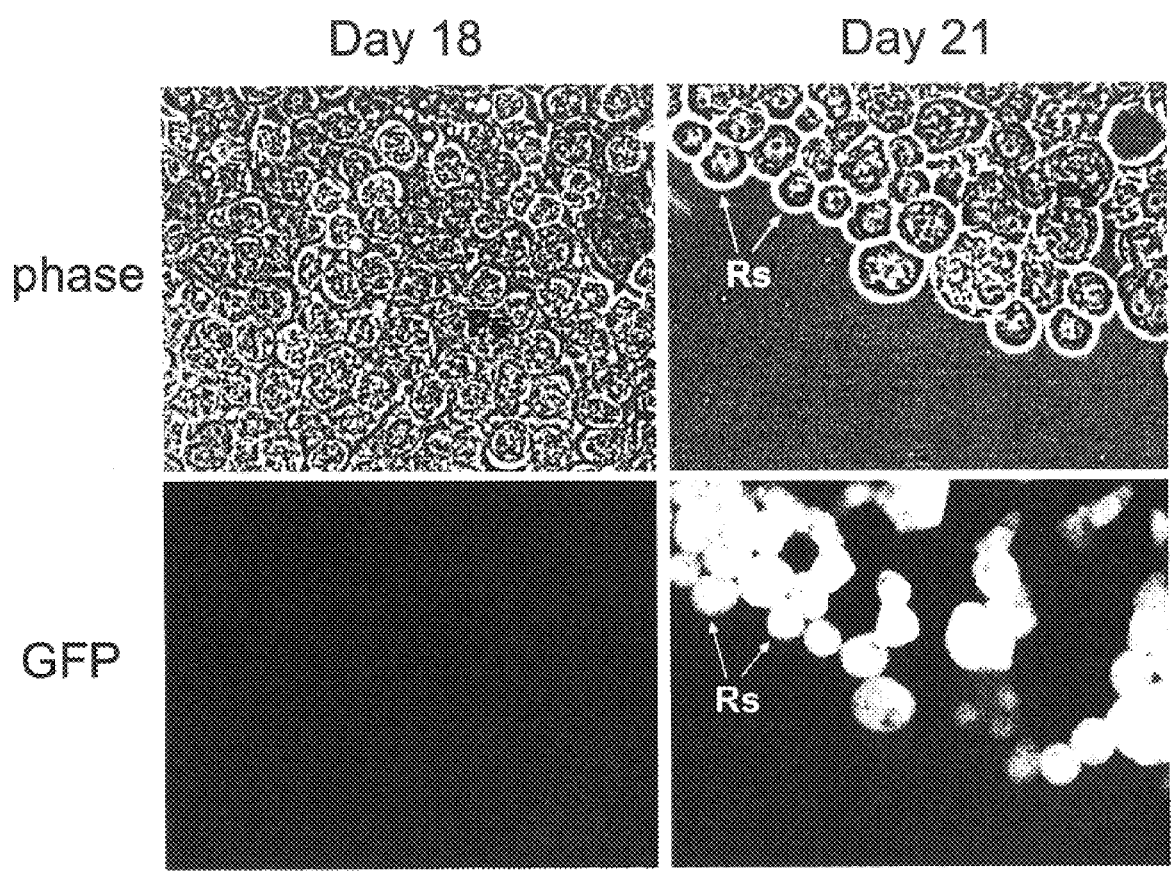

FIG. 7. Temporal onset of GFP expression under the −266 to +28 bp mSP-10 promoter control during puberty. The spermatogenic cells from 18 and 21 day old transgenic (−266SP10-gfp) mice were studied to examine the onset of transgenc expression during the first round of spermatogenesis in the developing testis. The 18 day old specimen shows late pachytene spermatocytes (day 18 phase), which do not produce any GFP (day 18 GFP). At day 21, however, the post-mciotic round spermatids (Rs), which are readily identified by their large nuclei and distinct nucleoli (day 21, phase), made their appearance. The GFP fluorescence is present in round spermatids of the −266SP10-gfp transgenic mice (day 21, GFP). Note the absence of fluorescence from the spermatocytes (day 21, Ps). The data indicate that the −266 to +28 bp SP-10 promoter fragment confined post-meiotic expression of GFP in the testis.

FIG. 8. Expression of GFP in the testis of SP-10-GFP transgenic mice. (A). Bright field and fluorescence views of the seminiferous tubules from non-transgenic [non-tr] and transgenic [tr] mice. The seminiferous tubules from the transgenic mice produced intense green fluorescence, whereas those from the non-transgenic littermate did not. (B) Identification of stages of the seminiferous epithelium and germ cell types expressing GFP in the SP-10-GFP transgenic mice. Using the transillumination assisted microdissection procedure, various stages of the seminiferous epithelium cycle were isolated and observed in order to determine the onset of GFP expression in the transgenic mice. Photomicrographs of stages XI–XII, I, V, and IX of the cycle, arranged vertically, arc shown in the figure. The three columns correspond [left to right] to phase-contrast, fluorescence and dual phase/fluorescence images of the same field. Stages XI–XII of the cycle are characterized by the meiotic reduction divisions. Step 12 spermatids (S 12), diplotene spermatocytes (Di), and meiotically dividing spermatocytes (MI) may be identified in the phase-contrast field. In the fluorescence image, only step 12 spermatids are positive for the GFP. Note, the lack of GFP signal in the spermatocytes. Stage I shows early postmciotic round spermatids (Rs) with round nuclei and prominent nucleoli, as well as early pachytene spermatocytes (P) with their condensed chromosomes, and step 13 spermatids (s13). The early round spermatids have initiated GFP synthesis at stage I. Due to the long half life of GFP, it persists within the cytoplasm of spermatids at later stages of development. For example, compare the dim fluorescence intensity in the round spermatids with the bright GFP color in step 13 spermatids seen in stage I. The expression of GFP continues through out haploid cell differentiation: Step 5 (sS), and step 15 (s15) spermatids at stage V, and step 9 (s9) spermatids at IX of the cycle are positive for GFP, whereas the pachytene spermatocytes (P) at these stages are negative for GFP. In sum, during spermatogenesis, under SP-10 promoter control, GFP production first begins in the early round spermatids, and accumulates in later steps of the spermatid development. It is evident that no GFP is produced in the spermatocytes.

Figure 9:
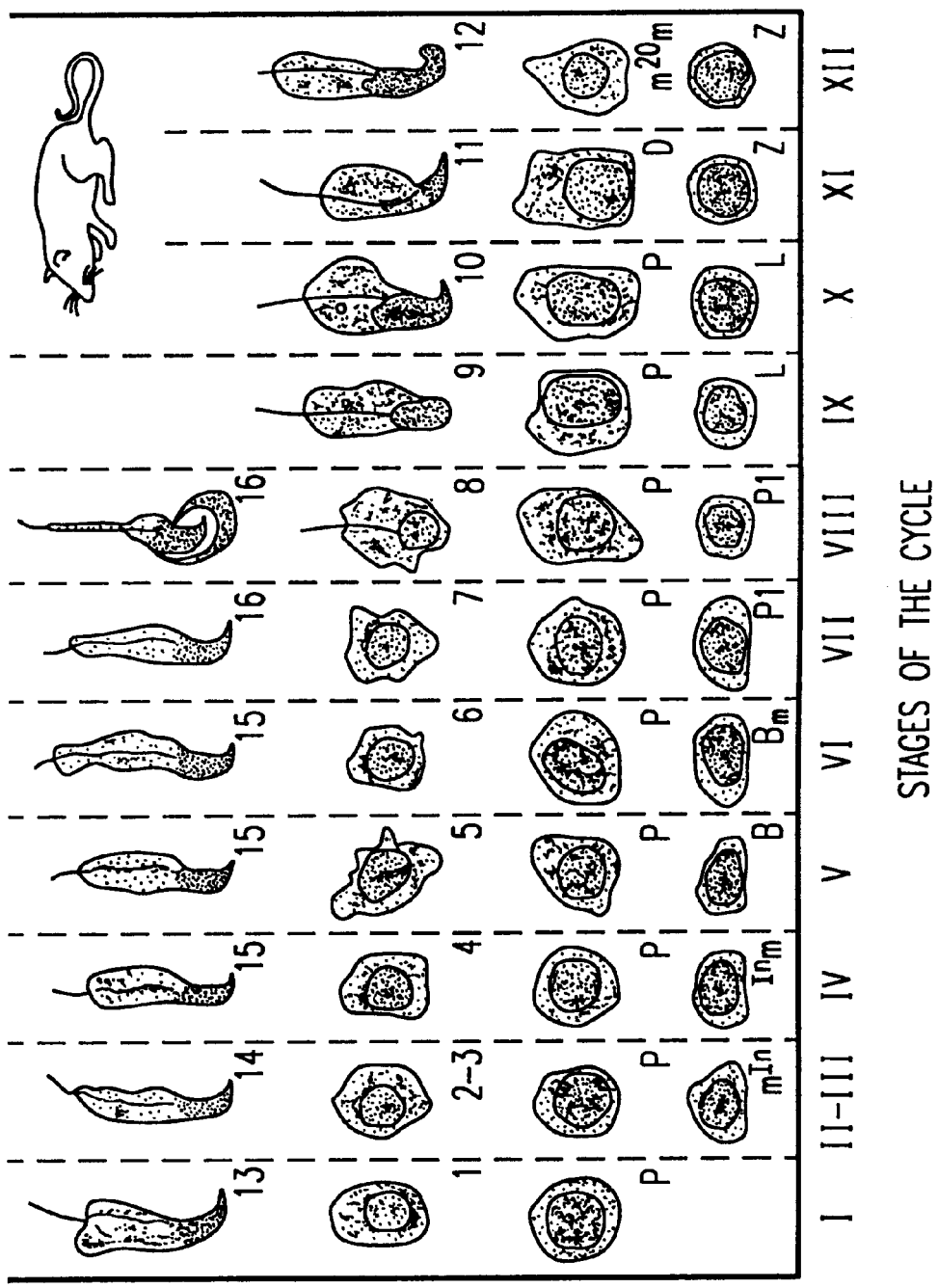

FIG. 9. Stages of the seminiferous epithelium cycle in the mouse. [Reproduced by permission of Cache River Press from L. D. Russel, R A. Ettlin, A. P. S. Hikim, E. D. Clegg, Histological and Histopathological Evaluation of the Testis (1990)]

FIG. 10. (A) Drawing of the transillumination pattern of mouse seminiferous tubule. A section of the tubule containing one whole wave of spermatogenesis showing the different light absorption zones is depicted here. (B) Diagrammatic representation of the transillumination-assisted microdissection procedure. [Adapted and modified with permission by Academic Press from Parvinen et. al, 1993, in *Methods in Toxicology*, Chapin & Heindel, eds., Vol 3, part A, 142, Academic Press, New York.]

Figure 11:
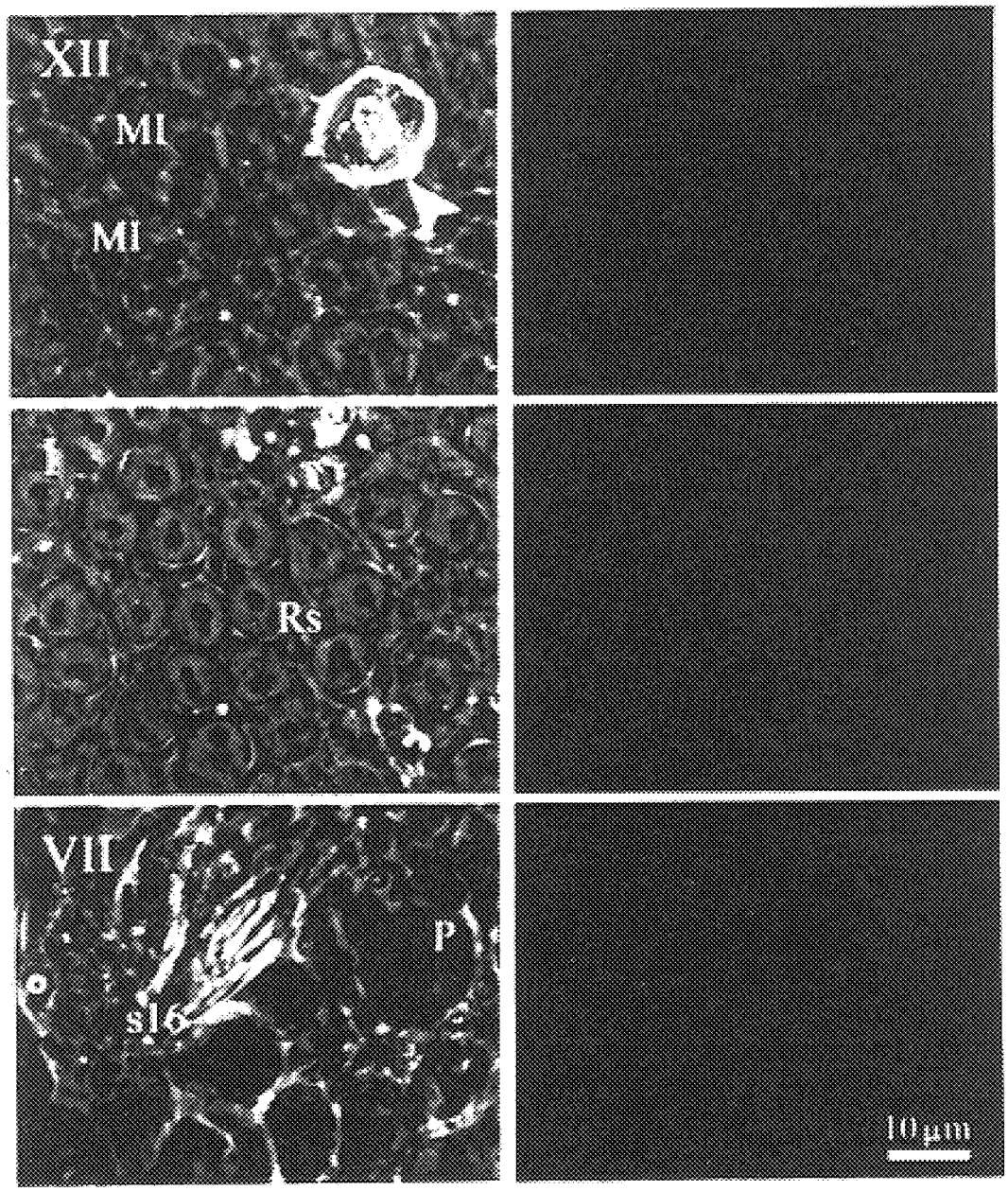

FIG. 11. Non-transgenic Littermates of the SP-10-GFP mice do not express GFP during the cycle of seminiferous epithelium. The left panel shows phase contrast micrographs from stages XII, I, and VII, the right panel is the fluorescence image of the same field. All cell types of the seminiferous epithelium including the haploid spermatids are GFP negative. MI, first meiotic division; Rs, round spermatids; P, pachytene spermatocytes; s16, step 16 spermatids. The arrowhead in stage XII micrograph denotes a degenerating spermatocyte in first meiotic division arrested at metaphase.

5. DETAILED DESCRIPTION OF THE INVENTION

The present invention provides compositions and methods for screening for compounds that modulate meiotic progression. The invention provides compositions comprising nucleotides from the mouse 5' regulatory region and transcriptionally active fragments thereof that control the expression of a testis-enriched protein, SP-10.

Described in detail below in Sections 5.1 and 5.2 are nucleotide sequences of the SP-10 regulatory region, and expression vectors, host cells and transgenic animals wherein a heterologous reporter gene, e.g., green fluorescent protein, controls the expression of the SP-10 regulatory region. In Section 5.3, methods for using such polynucleotides (i.e., regulatory regions of the SP-10 gene) and fusion protein products, (i.e., fusions of SP-10 with reporter gene constructs) for screening compounds that interact with the regulatory region of the SP-10 gene are described. This Section describes both in vivo and in vitro assays to screen small molecules, compounds, recombinant proteins, peptides, nucleic acids, antibodies etc. which bind to or modulate the activity of SP-10 reporter construct. Section 5.4 describes methods for the use of identified agonists and antagonists of SP-10 regulation for drug delivery or gene therapy. Finally, in Section 5.5, pharmaceutical compositions are described for using such agonists and antagonists to modulate sperm development and fertility. Methods and compositions are provided for contraception, sterilization, and treating infertility and cancer.

5.1 SP-10 POLYNUCLEOTIDE SEQUENCES

The present invention encompasses to polynucleotide sequences comprising the regulatory region, and transcriptionally active elements thereof, of the mouse SP-10 gene. In particular, the present invention relates to a polynucleotide comprising the sequence, shown in FIG. 3 (SEQ ID NO:1), that is located immediately 5' to the transcription start site of the murine SP-10 gene. A 298 bp fragment of this promoter, from −270 to +28 bp relative to the start of transcription of the SP-10 gene sequence is sufficient to direct round spermatid-specific transcription in vivo.

In specific embodiments, SP-10 regulatory nucleic acids comprise the genomic DNA sequences of SEQ ID NO:1 of FIG. 3, or transcriptionally active fragments thereof. The 5'-regulatory sequences of the SP-10 gene comprise the polynucleotide sequences located between the nucleotide in position −3000 and the nucleotide in position +120 of the nucleotide sequence of SEQ ID NO 1, more preferably between positions −408 and +28 of SEQ ID NO. 1, most preferably between −270 and +28 of SEQ ID NO. 1. Thus, in one embodiment of the invention, the regulatory region is a 298 bp fragment containing the minimal promoter sequence. In various embodiments, the polynucleotide may be 3000, 2000, 1000, 500, preferably approximately 500, more preferably 298 bp in length The invention further provides probes, primers, and fragments of the SP-10 regulatory region. In one embodiment, purified nucleic acids consisting of at least 8 nucleotides (i.e., a hybridizable portion) of an SP-10 gene sequence are provided; in other embodiments, the nucleic acids consist of at least 25 (contiguous) nucleotides, 50 nucleotides, 100 nucleotides, 200 nucleotides, or 500 nucleotides of an SP-10 sequence. In another embodiment, the nucleic acids are smaller than 35, 200 or 500 nucleotides in length. Nucleic acids can be single or double stranded. The invention also encompasses nucleic acids hybridizable to or complementary to the foregoing sequences. In specific aspects, nucleic acids are provided which comprise a sequence complementary to at least 10, 25, 50, 100, or 200 nucleotides or the entire regulatory region of an SP-10 gene.

The invention also encompasses:

(a) DNA vectors that contain any of the foregoing SP-10 regulatory sequences and/or their complements (i.e., antisense);

(b) DNA expression vectors that contain any of the foregoing SP-10 regulatory element sequences operatively associated with a reporter gene; and (c) genetically engineered host cells that contain any of the foregoing SP-10 regulatory element sequences operatively associated with a reporter gene such that the SP-10 regulatory element directs the expression of the reporter gene in the host cell.

Also encompassed within the scope of the invention are various transcriptionally active fragments of this regulatory region. A "transcriptionally active" or "transcriptionally functional" fragment of SEQ ID NO. 1 according to the present invention refers to a polynucleotide comprising a fragment of said polynucleotide which is functional as a regulatory region for expressing a recombinant polypeptide or a recombinant polynucleotide in a recombinant cell host. For the purpose of the invention, a nucleic acid or polynucleotide is "transcriptionally active" as a regulatory region for expressing a recombinant polypeptide or a recombinant polynucleotide if said regulatory polynucleotide contains nucleotide sequences which contain transcriptional information, and such sequences are operably associated to nucleotide sequences which encode the desired polypeptide or the desired polynucleotide.

In particular, the transcriptionally active fragments of the SP-10 promoter of the present invention encompass those fragments that are of sufficient length to promote transcription of a reporter gene when operatively linked to the SP-10 promoter sequence and transfected into a testes cell line. Typically, the promoter region is placed immediately 5' to, and is operatively associated with the coding sequence. As used herein, the term "operatively associated" refers to the placement of promoter sequence in immediately 5' (upstream) of the reporter gene, such that trans-acting factors required for initiation of transcription, such as transcription factors, polymerase subunits, and accessory proteins, can assemble at this region to allow RNA polymerase dependent transcription initiation of the reporter gene. The nucleotide sequence of this region is shown in FIG. 3 (SEQ ID NO:1).

In one embodiment, the polynucleotide sequence chosen may further comprise other nucleotide sequences, either from the SP-10 gene, or from a heterologous gene. In one embodiment, multiple copies of a promoter sequence, or a fragment thereof, may be linked to each other. For example, the promoter sequence, or a fragment thereof, may be linked to another copy of the promoter sequence, or another fragment thereof, in a head to tail, head to head, or tail to tail orientation. In another embodiment, a testes-specific enhancer may be operatively linked to the SP-10 promoter, or fragment thereof, and used to enhance transcription from the promoter construct.

Also encompassed within the scope of the invention are modifications of this nucleotide sequence without substantially affecting its transcriptional activities. Such modifications include additions, deletions and substitutions. In addition, any nucleotide sequence that selectively hybridizes to the complement of the sequence of SEQ ID NO: 1 under stringent conditions, and is capable of activating the expression of a coding sequence is encompassed by the invention. Exemplary moderately stringent hybridization conditions are as follows: prehybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 $\mu$g/ml denatured salmon sperm DNA. Filters are hybridized for 48 hours at 65° C. in prehybridization mixture containing 100 $\mu$g/ml denatured salmon sperm DNA and 5–20×10$^6$cpm of $^{32}$P-labeled probe. Washing of filters is done at 37° C. for 1 hour in a solution containing 2×SSC, 0.01% PVP, 0.01% Ficoll, and 0.01% BSA. This is followed by a wash in 0.1×SSC at 50° C. for 45 min before autoradiography. Alternatively, exemplary conditions of high stringency are as follows: eg., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3). Other conditions of high stringency which may be used are well known in the art.

The SP-10 promoter region, or transcriptionally functional fragments thereof, is preferably derived from a mammalian organism, and most preferably from mouse. Screening procedures which rely on nucleic acid hybridization make it possible to isolate any gene sequence from other organisms. The isolated polynucleotide sequence disclosed herein, or fragments thereof, may be labeled and used to screen a cDNA library constructed from mRNA obtained from appropriate cells or tissues (e.g., muscle tissue) derived from the organism of interest. The hybridization conditions used should be of a lower stringency when the cDNA library is derived from an organism different from the type of organism from which the labeled sequence was derived. Low stringency conditions are well know to those of skill in the art, and will vary depending on the specific organisms from which the library and the labeled sequence are derived. For guidance regarding such conditions see, for example, Sambrook et al., 1989, Molecular Cloning, A Laboratory Manual, Second Edition, Cold Spring Harbor Press, N.Y., and Ausabel et al., 1989, Current Protocols in Molecular Biology, Green Publishing Associates and Wiley Interscience, N.Y., each of which is incorporated herein by reference in its entirety. Further, a mammalian SP-10 promoter homologue may be isolated from, for example, bovine or other non-human nucleic acid, by performing polymerase chain reaction (PCR) amplification using two primer pools designed on the basis of the nucleotide sequence of the murine SP-10 promoter disclosed herein. The template for the reaction may be cDNA obtained by reverse transcription of the mRNA prepared from, for example, bovine or other non-human cell lines or tissue known to express the SP-10 gene. For guidance regarding such conditions see, for example, Innis et al. (Eds.) 1995, PCR Strategies, Academic Press Inc., San Diego; and Erlich (ed) 1992, PCR Technology, Oxford University Press, New York, each of which is incorporated herein by reference in its entirety.

Promoter sequences within the 5' non-coding regions of the SP-10 gene may be further defined by constructing nested 5' and/or 3' deletions using conventional techniques such as exonuclease III or appropriate restriction endonuclease digestion. The resulting deletion fragments can be inserted into the promoter reporter vector to determine whether the deletion has reduced or obliterated promoter activity, such as described, for example, by Coles et al. (Hum. Mol. Genet., 7:791–800, 1998). In this way, the boundaries of the promoters may be defined. If desired, potential individual regulatory sites within the promoter may be identified using site directed mutagenesis or linker scanning to obliterate potential transcription factor binding sites within the promoter individually or in combination. The effects of these mutations on transcription levels may be determined by inserting the mutations into cloning sites in promoter reporter vectors. This type of assays are well known to those skilled in the art (WO 97/17359, U.S. Pat. No. 5,374,544, EP 582 796, U.S. Pat. No. 5,698,389, U.S. Pat. No. 5,643,746, U.S. Pat. No. 5,502,176, and U.S. Pat. No. 5,266,488).

The SP-10 promoter regions and transcriptionally functional fragments thereof, and the fragments and probes described herein which serve to identify SP-10 promoter regions and fragments thereof, may be produced by recombinant DNA technology using techniques well known in the art. Methods which are well known to those skilled in the art can be used to construct these sequences, either in isolated form or contained in expression vectors. These methods include, for example, in vitro recombinant DNA techniques, synthetic techniques and in vivo genetic recombination. See, for example the techniques described Sambrook et al., 1989, supra, and Ausabel et al., 1989, supra; also see the techniques described in "Oligonucleotide Synthesis", 1984, Gait M. J. ed., IRL Press, Oxford, which is incorporated herein by reference in its entirety.

Alterations in the regulatory sequences can be generated using a variety of chemical and enzymatic methods which are well known to those skilled in the art. For example, regions of the sequences defined by restriction sites can be deleted. Oligonucleotide-directed mutagenesis can be employed to alter the sequence in a defined way and/or to introduce restriction sites in specific regions within the sequence. Additionally, deletion mutants can be generated using DNA nucleases such as Bal31, ExoIII, or S1 nuclease. Progressively larger deletions in the regulatory sequences are generated by incubating the DNA with nucleases for increased periods of time (see Ausubel el al., 1989, supra). The altered sequences are evaluated for their ability to direct expression of heterologous coding sequences in appropriate host cells. It is within the scope of the present invention that any altered regulatory sequences which retain their ability to direct expression of a coding sequence be incorporated into recombinant expression vectors for further use.

5.2 Analysis of Testis-specific Promoter Activity

The murine SP-10 gene promoter region shows selective tissue and cell-type specificity; i.e., it induces gene expression in testes cells, in particular in round spermatid cells. Thus, the regulatory region and transcriptionally active fragments thereof of the present invention may be used to induce expression of a heterologous gene in testes cells. The present invention relates to the use of the SP-10 gene promoter region to achieve tissue specific expression of a target gene. The activity and the specificity of the promoter of the SP-10 gene can further be assessed by monitoring the expression level of a detectable polynucleotide operably associated with the SP-10 promoter in different types of cells and tissues. As discussed hereinbelow, the detectable polynucleotide may be either a polynucleotide that specifically hybridizes with a predefined oligonucleotide probe, or a polynucleotide encoding a detectable protein.

5.2.1 SP-10 Promoter Driven Reporter Constructs

The regulatory polynucleotides according to the invention may be advantageously part of a recombinant expression vector that may be used to express a coding sequence, or reporter gene, in a desired host cell or host organism. The SP-10 promoter region of the present invention, and transcriptionally active fragments thereof, may be used to direct the expression of a heterologous coding sequence. In particular, the present invention encompasses murine species of the SP-10 promoter region. In accordance with the present invention, transcriptionally active fragments of the SP-10 promoter region encompass those fragments of the promoter which are of sufficient length to promote transcription of a reporter coding sequence to which the fragment is operatively linked.

A variety of reporter gene sequences well known to those of skill in the art can be utilized, including, but not limited to, genes encoding fluorescent proteins such as green fluorescent protein (GFP), enzymes (e.g CAT, beta-galactosidase, luciferase), or antigenic markers. For convenience, enzymatic reporters and light-emitting reporters analyzed by colorometric or fluorometric assays are preferred for the screening assays of the invention.

In one embodiment, for example, a bioluminescent, chemiluminescent or fluorescent protein can be used as a light-emitting reporter in the invention. Types of light-emitting reporters, which do not require substrates or cofactors, include but are not limited to the wild-type green fluorescent protein (GFP) of Victoria aequoria (Chalfie et al., 1994, Science 263:802–805), and modified GFPs (Heim et al., 1995, Nature 373:663–4; PCT publication WO 96/23810). Transcription and translation of this type of reporter gene leads to the accumulation of the fluorescent protein in test cells, which can be measured by a fluorimeter, or a flow cytometer, for example, by methods that are well known in the art (see, e.g., Lackowicz, 1983, Principles of Fluorescence Spectroscopy, Plenum Press, New York). An example of the construction of the SP-10-GFP reporter construct is described in the example presented in Section 6, below, while the Example presented in Section7 demonstrate the successful measurement of such reporter gene sequences to assay the expression of SP-10 during spermatid development.

Another type of reporter gene that may be used are enzymes that require cofactor(s) to emit light, including but not limited to, Renilla luciferase. Other sources of luciferase are also well known in the art, including but not limited to, the bacterial luciferase (luxAB gene product) of *Vibrio harveyi* (Karp, 1989, Biochim. Biophys. Acta 1007:84–90; Stewart et al. 1992, J. Gen. Microbiol, 138:1289–1300), and the luciferase from firefly, *Photinus pyralis* (De Wet et al. 1987, Mol. Cell. Biol. 7:725–737), which can be assayed by light production (Miyamoto et al., 1987, J. Bacteriol. 169:247–253; Loessner et al. 1996, Environ. Microbiol. 62:1133–1140; and Schultz & Yarus, 1990, J. Bacteriol. 172:595–602).

Reporter genes that can be analyzed using colorimetric analysis include, but are not limited to β-galactosidase (Nolan et al. 1988, Proc. Natl. Acad. Sci. USA 85:2603–07), β-glucuronidase (Roberts et al. 1989, Curr. Genet. 15:177–180), luciferase (Miyamoto et al., 1987, J. Bacteriol. 169:247–253), or β-lactamase. In one embodiment, the reporter gene sequence comprises a nucleotide sequence which encodes a LacZ gene product, β-galactosidase. The enzyme is very stable and has a broad specificity so as to allow the use of different histochemical, chromogenic or fluorogenic substrates, such as, but not limited to, 5-bromo-4-chloro-3-indoyl-β-D-galactoside (X-gal), lactose 2,3,5-triphenyl-2H-tetrazolium (lactose-tetrazolium), and fluorescein galactopyranoside (see Nolan et al., 1988, supra).

In another embodiment, the product of the *E. coli* β-glucuronidase gene (GUS) can be used as a reporter gene (Roberts et al. 1989, Curr. Genet. 15:177–180). GUS activity can be detected by various histochemical and fluorogenic substrates, such as X-glucuronide (Xgluc), and 4-methylumbelliferyl glucuronide.

In addition to reporter gene sequences such as those described above, which provide convenient colorimetric responses, other reporter gene sequences, such as, for example, selectable reporter gene sequences, can routinely be employed. For example, the coding sequence for chloramphenicol transacetylase (CAT) can be utilized, leading to SP-10 promoter-dependent expression of chloramphenicol resistant cell growth. The use of CAT and the advantages of a selectable reporter gene are well known to those skilled in the art (Eikmanns et al. 1991, Gene 102:93–98). Other selectable reporter gene sequences can also be utilized and include, but are not limited to gene sequences encoding polypeptides which confer zeocin (Hegedus et al. 1998, Gene 207:241–249) or kanamycin resistance (Friedrich & Soriano, 1991, Genes. Dev. 5:1513–1523).

Other reporter genes, such as toxic gene products, potentially toxic gene products, and antiproliferation or cytostatic gene products, can also be used. In another embodiment, the detectable reporter polynucleotide may be either a polynucleotide that specifically hybridizes with a predefined oligonucleotide probe, or a polynucleotide encoding a detectable protein, including an SP-10 polypeptide or a fragment or a variant thereof. This type of assay is well known to those skilled in the art (U.S. Pat. No. 5,502,176 and U.S. Pat. No. 5,266,488).

SP-10 driven reporter constructs can be constructed according to standard recombinant DNA techniques (see e.g., Methods in Enzymology, 1987, volume 154, Academic Press; Sambrook et al. 1989, Molecular Cloning—A Laboratory Manual, 2nd Edition, Cold Spring Harbor Press, New York; and Ausubel et al. Current Protocols in Molecular Biology, Greene Publishing Associates and Wiley Interscience, New York, each of which is incorporated herein by reference in its entirety).

Methods for assaying promoter activity are well-known to those skilled in the art (see Sambrook et al., Molecular Cloning A Laboratory Manual, Cold Spring Harbor Laboratory, Cold Spring Harbor, N.Y., 1989). An example of a typical method that can be used involves a recombinant vector carrying a reporter gene and genomic sequences from the SP-10 genomic sequence of SEQ ID NO:1. Briefly, the expression of the reporter gene (for example, green fluorescent protein, luciferase, β-galactosidase, or chloramphenicol acetyl transferase) is detected when placed under the control of a biologically active polynucleotide fragment. Genomic sequences located upstream of the first exon of the gene may be cloned into any suitable promoter reporter vector. For example, a number of commercially available vectors can be engineered to insert the SP-10 regulatory region of the invention for expression in mammalian host cells. Non-limiting examples of such vectors are pSEAPBasic, pSEAP-Enhancer, pβgal-Basic, pβgal-Enhancer, or pEGFP-1 Promoter Reporter vectors (Clontech, Palo Alto, Calif.) or pGL2-basic or pGL3-basic promoterless luciferase reporter gene vector (Promega, Madison, Wis.). Each of these promoter reporter vectors include multiple cloning sites positioned upstream of a reporter gene encoding a readily assayable protein such as secreted alkaline phosphatase, green fluorescent protein, luciferase, or β-galactosidase. The sequences upstream the first SP-10 exon are inserted into the cloning sites upstream of the reporter gene in both orientations and introduced into an appropriate host cell. The level of reporter protein is assayed and compared to the level obtained with a vector lacking an insert in the cloning site. The presence of an elevated expression level in the vector containing the insert with respect the control vector indicates the presence of a promoter in the insert.

Expression vectors that comprise an SP-10 gene promoter region may further contain a gene encoding a selectable marker. A number of selection systems may be used, including but not limited to, the herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes, which can be employed in tk⁻, hgprt⁻ or aprt⁻ cells, respectively. Also, antimetabolite resistance can be used as the basis of selection for dhfr, which confers resistance to methotrexate (Wigler et al., 1980, Proc. Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147) genes. Additional selectable genes include trpB, which allows cells to utilize indole in place of tryptophan; hisD, which allows cells to utilize histinol in place of histidine (Hartman & Mulligan, 1988, Proc. Natl. Acad. Sci. USA 85:8047); ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.) and glutamine synthetase (Bebbington et al., 1992, Biotech 10:169).

5.2.2 Characterization of Transcriptionally Active Promoter Fragments

The fusion construct comprising an SP-10 promoter region, or a fragment thereof, can be assayed for transcriptional activity. As a first step in promoter analysis, the transcriptional start point (+1 site) of the testis-specific gene under study has to be determined using primer extension assay and/or RNAase protection assay, following standard methods (Sambrook et al., 1989, Molecular Cloning: A Laboratory Manual, Cold Spring Harbor, Cold Spring Harbor Press). The DNA sequence upstream of the +1 site is generally considered as the promoter region responsible for gene regulation. To begin testing for promoter activity, a −3 kb to +20 bp promoter region (where +1 is the transcriptional start point) may be cloned upstream of the reporter gene coding region. Two or more additional reporter gene constructs may also be made which contain 5' truncated version of the promoter to aid in identification of the region responsible for testis-specific expression. The choice of the type of reporter gene is made based on the application.

In the preferred embodiment a GFP reporter gene construct is used. The application of green fluorescent protein (GFP) as a reporter is particularly useful in the study of testis-specific gene promoters. A major advantage of using GFP as a reporter lies in the fact that GFP can be detected in freshly isolated spermatogenic cells without the need for substrates. When combined with the transillumination-assisted microdissection technique, expression of GFP in the testis permits precise identification of the germ cell type and the stage of the seminiferous epithelium cycle at which the putative promoter is active.

For promoter analysis in transgenic mice, GFP that has been optimized for expression in mammalian cells is preferred. The promoterless cloning vector pEGFP1 (Clontech, Palo Alto, Calif.) encodes a red shifted variant of the wild-type GFP which has been optimized for brighter fluorescence and higher expression in mammalian cells (Cormack et al., 1996, Gene 173:33; Haas et al., 1996, Curr. Biol. 6:315). Moreover, since the maximal excitation peak of this enhanced GFP (EGFP) is at 488 nm, commonly used filter sets such as fluorescein isothiocyanate (FITC) optics which illuminate at 450–500 nm can be used to visualize GFP fluorescence. pEGFP1 proved to be useful as a reporter vector for promoter analysis in transgenic mice (Okabe et al., 1997, FEBS Lett. 407:313).

Putative promoter fragments can be prepared (usually from a parent phage clone containing 8–10 kb genomic DNA including the promoter region) for cloning using methods known in the art. In one embodiment, for example, promoter fragments are cloned into the multiple cloning site of a GFP reporter vector. In one embodiment, restriction endonucleases are used to excise the promoter fragments to be inserted into the reporter vector. For example, if EcoRI and BamHI sites were present at −3 kb and +20 bp positions of the promoter fragment, then the −3 kb to +20 bp fragment can be generated by digestion with Eco RI and Bam HI. However, the feasibility of this method depends on the availability of proper restriction endonuclease sites in the promoter fragment. In a preferred embodiment, the required promoter fragment is amplified by polymerase chain reaction (PCR; Saiki et al., 1988, Science 239:487) using oligonucleotide primers bearing the appropriate sites for restriction endonuclease cleavage. The sequence necessary for restriction cleavage is included at the 5' end of the forward and reverse primers which flank the promoter fragment to be amplified. After PCR amplification, the appropriate ends are generated by restriction digestion of the PCR product. The promoter fragments, generated by either method, are then ligated into the multiple cloning site of the reporter vector following standard cloning procedures (Sambrook et al.,1989, supra). It is recommended that the DNA sequence of the PCR generated promoter fragments in the constructs be verified prior to generation of transgenic mice. The resulting reporter gene construct will contain the putative promoter fragment located upstream of the reporter gene open reading frame, e.g., GFP eDNA.

For microinjection of fertilized eggs, a linear DNA fragment (the transgene) containing the promoter, the reporter gene, and the polyadenylation signals, is excised from the reporter gene construct. The transgene may be gel purified by methods known in the art, for example, by the electroelution method. Following electroelution of gel fragments, any traces of impurities are further removed by passing through Elutip D column (Schleicher & Schuell, Dassel, Germany).

In the preferred embodiment, the following protocol is used. Fifty to 100 pg of the reporter gene construct is digested using appropriate restriction endonucleases to release the transgene fragment. The restriction endonuclease cleaved products are resolved in a 1% (w/v) agarose gel containing 0.5 ug/ml ethidium bromide and TAE buffer (1X: 0.04 M Tri-acetate, 0.001 M EDTA, pH 8.0) at 5–6 V/cm. The transgene band is located by size using a UV transilluminator, preferably using long-wavelength UV lamp to reduce nicking of DNA, and the gel piece containing the required band carefully excised. The gel slice and 1 ml of 0.5×TAE buffer is added to a dialysis bag, which has been boiled in 1 mM EDTA, pH 8.0 for 10 minutes (Sambrook et al., 1989, supra) and the ends are fastened. The dialysis bag containing the gel piece is submerged in a horizontal gel electrophoresis chamber containing 0.5×TAE buffer, and electrophoresed at 5–6 V/cm for 45 minutes. The current flow in the electrophoresis chamber is reversed for one minute before stopping the run to release the DNA which may be attached to the wall of the dialysis tube. The TAE buffer containing the electroeluted DNA from the dialysis bag is collected in a fresh eppendorf tube. The gel piece may be observed on the UV transilluminator to ascertain that the electroelution of the DNA is complete.

The electroeluted DNA sample is further purified by passing through Elutip D columns. The matrix of the column is prewashed with 1–2 ml of High salt buffer (1.0 M NaCl, 20 mM Tris. Cl, 1.0 mM EDTA, pH 7.5), followed by a wash with 5 ml of Low salt buffer (0.2 M NaCl, 20 mM Tris. Cl, 1.0 mM EDTA, pH 7.5). A 5 ml syringe is used to apply solutions to the Elutip D column, avoiding reverse flow. The solution containing the electroeluted DNA is loaded slowly. The column is washed with 2–3 ml of Low salt buffer and the DNA is eluted in 0.4 ml of High salt buffer. Two volumes of cold 95% ethanol is added to precipitate DNA. The DNA is collected by centrifugation in a microcentrifuge at 14,000 g for 10 minutes, carefully removing the alcohol without disrupting the DNA pellet. The pellet is washed at least twice with 70% (v/v) ethanol, and dried. The washing and drying steps are important, as residual salt and ethanol are lethal to the developing embryos. The DNA is resuspend in the injection buffer (10 mM TM, 0.1 mM EDTA, pH 7.5 prepared with Milli-Q quality water). The concentration of the purified transgene DNA fragment is determined by measuring the optical density at $A_{260}$ ($A_{260}$ =1 for 50 $\mu$g/ml DNA) using a spectrophotometer. DNA prepared in this manner is suitable for microinjection into fertilized mouse eggs.

The present invention provides for transgenic animals that carry a transgene such as a reporter gene under the control of the SP-10 regulatory region or transcriptionally active fragments thereof in all their cells, as well as animals that carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (1992, Proc. Natl. Acad. Sci. USA 89:6232–6236). When it is desired that the transgene be integrated into the chromosomal site of the endogenous corresponding gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene.

5.2.3 Testis-specific Promoter Analysis Using Transgenic Mice

The mammalian SP-10 regulatory region can be used to direct expression of a reporter coding sequence in transgenic animals. Animals of any species, including, but not limited to, mice, rats, rabbits, guinea pigs, pigs, micro-pigs, goats, sheep, and non-human primates, e.g., baboons, monkeys and chimpanzees may be used to generate transgenic animals. The term "transgenic," as used herein, refers to animals expressing SP-10 gene sequences from a different species (e.g., mice expressing SP-10 sequences), as well as animals that have been genetically engineered to overexpress endogenous (i.e., same species) SP-10 sequences or animals.

Any technique known in the art may be used to introduce a transgene under the control of the SP-10 regulatory region into animals to produce the founder lines of transgenic animals. Such techniques include, but are not limited to, pronuclear microinjection (Hoppe & Wagner, 1989, U.S. Pat. No. 4,873,191); nuclear transfer into enucleated oocytes of nuclei from cultured embryonic, fetal or adult cells induced to quiescence (Campbell et al., 1996, Nature 380:64–66; Wilmut et al., Nature 385:810–813); retrovirus gene transfer into germ lines (Van der Putten et al., 1985, Proc. Natl. Acad. Sci., USA 82:6148–6152); gene targeting in embryonic stem cells (Thompson et al., 1989, Cell 65:313–321); electroporation of embryos (Lo, 1983, Mol. Cell. Biol. 31:1803–1814); and sperm-mediated gene transfer (Lavitrano et al., 1989, Cell 57:717–723; see, Gordon, 1989, Transgenic Animals, Intl. Rev. Cytol. 115:171–229).

In the preferred embodiment, the purified transgene fragment is microinjected into the male pronuclei of fertilized eggs obtained from B6 CBA females by standard methods (Hogan, 1986, Manipulating the Mouse Embryo, A Laboratory Manual. Cold Spring Harbor Laboratory Press, Cold Spring Harbor, N.Y.). Tail biopsies are collected from three week old pups and genomic DNA isolated (Hogan, 1986, supra). Founder transgenic mice are identified by PCR analysis of genomic DNA, using the following GFP primers:

5' primer: 5'ATGGTGAGCAAGGGCGAGGAGCTG (SEQ ID NO. 4)

3' primer: CTTGTACAGCTCGTCCATGCCGAG (SEQ ID NO. 5)

which are complementary to the GFP CDNA (a 716 bp region between bp 97 through 813 in pEGFP1I vector, Genbank accession number U55761) in the reporter gene construct. Preferably, the PCR reaction is carried out in a volume of 100 $\mu$l containing 1 $\mu$g of genomic DNA, in 1×reaction buffer supplemented with 0.2 mM dNTPs, 2 mM MgCl$_2$, 600 $\mu$M each of primer, and 2.5 units of Taq polymerase (Promega, Madison, Wis.). Each of the PCR cycles consists of denaturation at 94° C. for 1 min, annealing at 54° C. for 1 min, and extension at 72° C. for 1 min. The founder mice may be identified by the presence of the 716 bp GFP PCR product. The founder mice are then mated with C57B1 partners to generate transgenic F$_1$ lines of mice.

5.2.4 Analysis of Transgenic Mice Expressing GFP

Once transgenic animals have been generated, the transcriptional activities of the SP-10 regulatory region may be assayed utilizing standard techniques. A preferred embodiment of such an analysis is provided hereinbelow, and a detailed analysis of SP-10 promoter-GFP expression is provided as a working example in Section 7.

Sexually mature F$_1$ transgenic males are analyzed to address the question whether the putative promoter conferred the expected spatial and temporal expression pattern to the reporter gene product. Detection of reporter gene in the testis using the transillumination-assisted microdissection technique permits precise identification of the germ cell type and the stage of the seminiferous epithelium cycle at which the putative promoter is active.

In a preferred embodiment, GFP is used as a reporter construct. Fluorescent labeling of cells by GFP allows a rapid screening for tissues in which the transgene is expressed, which can be performed using a fluorescence microscope equipped with FITC optics (Sambrook et al., 1989, supra). In alternative embodiments, screening may also be accomplished by standard techniques known in the art, such as Southern blot analysis or PCR techniques to analyze animal tissues to assay whether integration of the transgene has taken place. The level of mRNA expression of the transgene in the tissues of the transgenic animals may also be assessed using techniques that include, but are not limited to, Northern blot analysis of tissue samples obtained from the animal, in situ hybridization analysis, and RT-PCR. Samples of transgene-expressing tissue, may also be evaluated immunocytochemically using antibodies specific for the transgene product.

In a preferred embodiment, the following method is used to screen tissues for promoter-driven GFP reporter gene expression. Six to 8 week old transgenic male mice are sacrificed by CO$_2$ inhalation, or any other acceptable procedure known in the art. Testis, liver, heart, kidney, lung, spleen, muscle, intestine, and brain are removed into separate Petri dishes containing sterile PBS at 37° C. A small piece (1–2 mm) is cut from each tissue, placed on a glass slide in 30 $\mu$l of PBS, and minced finely with forceps. A coverslip is gently placed on top, and the edges sealed using paraffin oil to prevent evaporation. The slides are observed at 10–40×, under fluorescence optics. The cells from the tissues in which GFP gene is expressed fluoresce bright green. The tissue samples from a non-transgenic littermate processed in the same way are observed, serving as a negative control for autofluorescence.

The seminiferous tubules of the testis is specifically microdissected to analyze stage-specific expression of the SP-10 transgene. A number of basic tools are required for transillumination-assisted microdissection: a stereomicroscope with transmitted light and magnification ranging from 1-to-10×, nonnal scissors, two fine forceps, and small iridectomy scissors. The procedure is shown schematically in FIG. 10B. First, the testis is decapsulated and transfered to a Petri dish containing Testis Isolation Medium (TIM, 105 mM NaCl, 45 mM KCl, 1.2 mM MgSO$_4$, 6.0 mM Na$_2$HPO$_4$, 0.7 mM glucose, pH 7.2, 0.05% phenol red, 1.2 mM CaCl$_2$) which has been prewarmed at 37° C. The Petri dish is placed under a stereomicroscope with transmitted light. Next, the tubules are gently pulled apart with fine forceps using a low magnification (1–3×) until transillumination pattern of parts of individual tubules can be observed . A long segment of the tubule is separated from the rest of the testis using small iridectomy scissors and fine forceps. An approximately 2 cm segment running from the start of the pale light absorption zone to the end of dark zone, a wave of seminiferous epithelium, is preferentially isolated. A clear difference in tubular transillumination can be found at stage VIII, where the dark zone abruptly ceases.

The long segment of the tubule is transfered to a clear part of the Petri dish and different light absorption zones can be identified using a higher magnification (3–10×). A desired zone or stage of the cycle can then be localized, and a short (~2 mm) tubule segment is cut from this region and transfered in an aliquot of 30–40 μl of TIM or tissue culture medium (Hams F12/Dulbecco's MEM 1:1) onto a clean objective slide and covered with a 22×22 mm coverslip. The weight of the coverslip pushes the cells out of the tubule segment and a slightly flattened monolayer of cells is formed. This process can be aided by absorbing extra medium from beneath the coverslip using a soft tissue paper. Different germ cell populations flow out from a tubule segment in an order dictated by the localization of the germ cell types within a particular segment of the seminiferous epithelium. Cells close to the lumen of the seminiferous tubule, including postmeiotic round spermatids and elongating spermatids are the first cells to appear. These are followed by meiotic cells such as pachytene spermatocytes and lastly, different types of spermatogonia and the Sertoli cells flow out. It is important to spread the cells as a monolayer, avoiding the absorption of too much medium from under the coverslip, as this may cause the cells to disrupt. For live cell analysis, the edges of the coverslip are sealed with mineral oil to prevent gas exchange and drying of the sample. Sealing also prevents cell movement under the coverslip. The sample can next be analyzed with phase-contrast and/or fluorescence microscope.

Figure 8A:
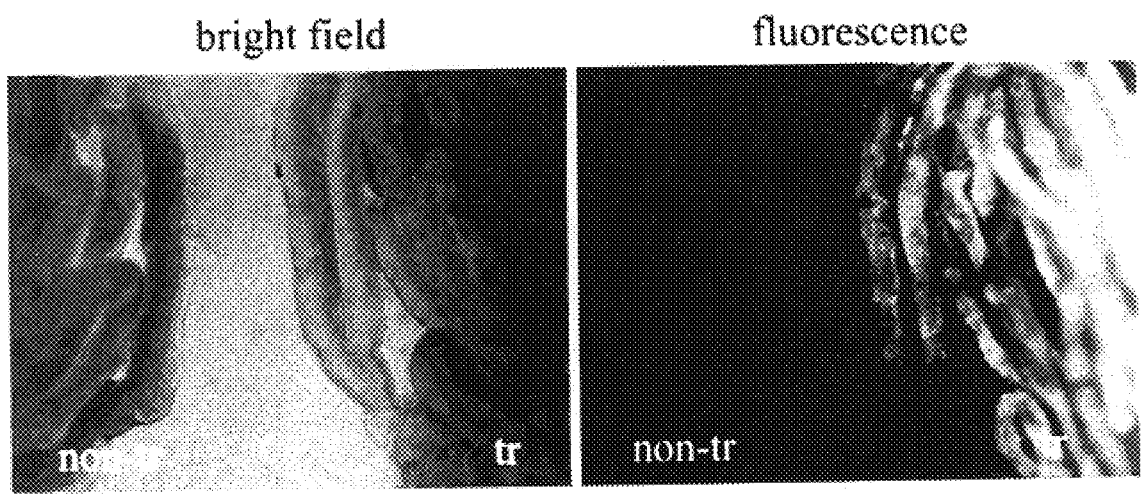
Figure 8B:
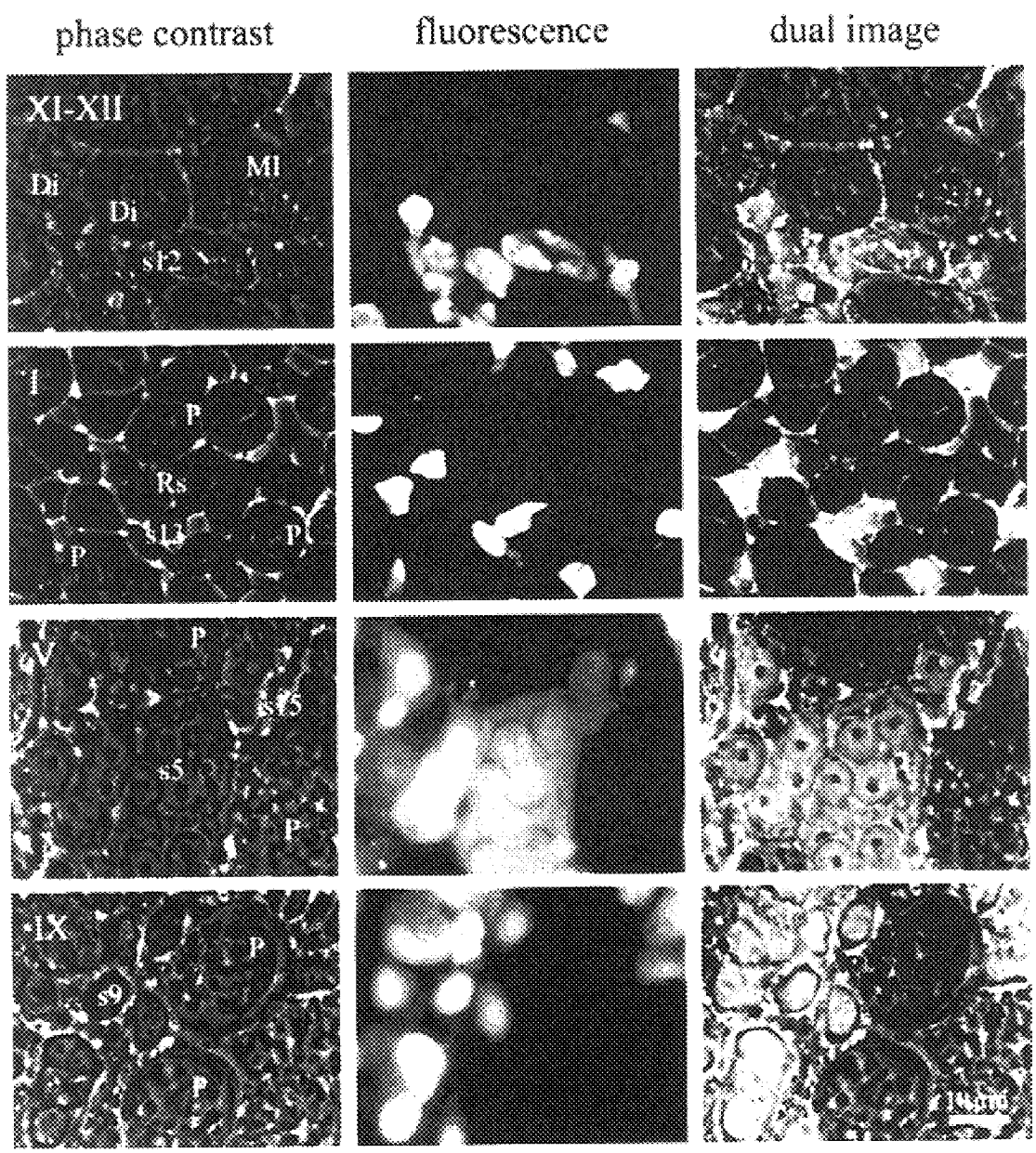

Identification of fluorescent germ cells at various stages of spermatogenesis indicates the stage of expression of the SP-10 promoter fragment, or other fragment of interest. Stage-specific spermatid expression can be analyzed by sample morphologies (photomicrographs representing stages XI–XII, I, V, IX from transgenic mice are shown in FIG. 8B). The stages can be identified based on the morphology of the developing acrosomes and the nuclei of the spermatids. At stage I, two steps of spermatids may be identified; early post-meiotic step 1, and elongated step 13 spermatids. The step 1 spermatids have round nuclei with prominent nucleoli, whereas the step 13 spermatids have prominent hook shaped nuclei (see stage I, s13 in FIG. 8B). The step 5 spermatids at stage V are characterized by the developing acrosomic system spreading over the nuclear envelope. At stage IX, the only haploid cells are step 9 spermatids with elongated nuclei. Stage XII is characterized by the presence of meiotic divisions. As a control, analysis of the stages of non-transgenic littermates (control mice) show fluorescent cells at any stages of the cycle.

5.3 Screening Assays

Compounds that interfere with acrosomal biogenesis, which marks the beginning of the terminal phase of male germ cell differentiation, can provide therapies targeting defects in spermatogenesis leading to azospermia and infertility. Such compounds may be used to interfere with spermatogenisis and may be useful as contraceptives or for sterilization. Compounds that stimulate promoter activity may be used to restore spermatogenisis for treatment of infertility.

Development of spermatogenic cell lines has been difficult due to the uncertainty about the phenotype of the "differentiated" spermatogenic cell. Thus, a mouse model for spermagenesis has proven useful for developing a system for screening agents that modulate fertility. Transgenic animals or spermatogenic cells containing an SP-10 promoter, or fragment thereof, operably linked to a reporter gene, can be used as systems for the screening of agents that modulate SP-10 transcriptional activity. In a preferred embodiment, transformed spermatogonial or spermatocyte cell lines derived from the SP-10-GFP mice may be conveniently monitored for progression through meiosis. Similarly, GFP producing germ cells may be easily tracked in spermatogonial stem cell transplantation experiments, to identify the donor cell line. In addition, SP-10-GFP mice may provide an experimental model both in vivo and in vitro to develop new methods of male contraception by targeting drugs to cause arrest in spermatogenesis.

The present invention encompasses screening assays designed to identify compounds that modulate SP-10 promoter activity. The present invention encompasses in vitro and cell-based assays, as well as in vivo assays in transgenic animals. As described hereinbelow, compounds to be tested may include, but are not limited to, oligonucleotides, peptides, proteins, small organic or inorganic compounds, antibodies, etc.

In one preferred embodiment, primary cultures of germ cells containing a mammalian SP-10 promoter operatively linked to a heterologous gene, such as SP-10-GFP, is used to develop assay systems to screen for compounds which can inhibit sequence-specific DNA-protein interactions. Such methods comprise contacting a compound to a cell that expresses a gene under the control of a SP-10 promoter or a transcriptionally active fragment thereof, measuring the level of the gene expression or gene product activity and comparing this level to the level of gene expression or gene product activity produced by the cell in the absence of the compound, such that if the level obtained in the presence of the compound differs from that obtained in its absence, a compound capable of modulating the expression of the mammalian SP-10 gene or promoter activity has been identified. Alterations in gene expression levels may be by any number of methods known to those of skill in the art e.g., by assaying for reporter gene activity, assaying cell lysates for mRNA transcripts, e.g. by Northern analysis, or using other methods known in the art for assaying for gene products expressed by the cell.

In another embodiment, the microdissection and transillumination of seminiferous tubules method described above in Section 5.2.4 offers a rapid assay for monitoring effects of putative contraceptive compounds on spermiogenesis in transgenic animals containing an sp10 promoter-driven reporter gene. In this embodiment, a test agent is delivered to the transgenic animal by any of a variety of methods. Methods of introducing a test agent may include oral, intradermal, intramuscular, intraperitoneal, intravenous, subcutaneous, intranasal, and via scarification (scratching through the top layers of skin, e.g., using a bifurcated needle) or any other standard routes of drug delivery. The effect of such test compounds on the spermatogenesis can be analyzed by the microdissection and transillumination of seminiferous tubules method described above in Section 5.2.4. If the level of reporter gene expression observed or measured in the presence of the compound differs from that obtained in its absence, a compound capable of modulating the expression of the mammalian SP-10 gene or promoter activity has been identified.

In various embodiments of the invention, compounds that may be used in screens for modulators of fertility include peptides, small molecules, both naturally occurring and/or synthetic (e.g., libraries of small molecules or peptides), cell-bound or soluble molecules, organic, non-protein molecules, recombinant molecules that may have SP-10 promoter binding capacity and, therefore, may be candidates for pharmaceutical agents.

Alternatively, the proteins and compounds include endogenous cellular components which interact with SP-10 promoter sequences in vivo. Cell lysates or tissue homogenates may be screened for proteins or other compounds which bind to the SP-10 promoter, or fragment thereof. Such endogenous components may provide new targets for pharmaceutical and therapeutic interventions.

In one embodiment, libraries can be screened. Many libraries are known in the art that can be used, e.g., peptide libraries, chemically synthesized libraries, recombinant (e.g., phage display libraries), and in vitro translation-based libraries. In one embodiment of the present invention, peptide libraries may be used to screen for agonists or antagonists of SP-10-linked reporter expression. Diversity libraries, such as random or combinatorial peptide or non-peptide libraries can be screened for molecules that specifically modulate SP-10 promoter activity. Random peptide libraries consisting of all possible combinations of amino acids attached to a solid phase support may be used to identify peptides that are able to activate or inhibit SP-10 promoter activities (Lam, K. S. et al., 1991, Nature 354: 82–84). The screening of peptide libraries may have therapeutic value in the discovery of pharmaceutical agents that stimulate or inhibit the expression of SP-10 by interaction with the promoter region.

Examples of chemically synthesized libraries are described in Fodor et al., 1991, Science 251:767–773; Houghten et al., 1991, Nature 354:84–86; Lam et al., 1991, Nature 354:82–84; Medynski, 1994, BioTechnology 12:709–710; Gallop et al., 1994, J. Medicinal Chemistry 37(9):1233–1251; Ohlmeyer et al., 1993, Proc. Natl. Acad. Sci. USA 90:10922–10926; Erb et al., 1994, Proc. Natl. Acad. Sci. USA 91:11422–11426; Houghten et al., 1992, Biotechniques 13:412; Jayawickreme et al., 1994, Proc. Natl. Acad. Sci. USA 91:1614–1618; Salmon et al., 1993, Proc. Natl. Acad. Sci. USA 90:11708–11712; PCT Publication No. WO 93/20242; and Brenner and Lerner, 1992, Proc. Natl. Acad. Sci. USA 89:5381–5383.

Examples of phage display libraries are described in Scott and Smith, 1990, Science 249:386–390; Devlin et al., 1990, Science, 249:404–406; Christian, et al., 1992, J. Mol. Biol. 227:711–718; Lenstra, 1992, J. Immunol. Meth. 152:149–157; Kay et al., 1993, Gene 128:59–65; and PCT Publication No. WO 94/18318 dated Aug. 18, 1994.

By way of examples of non-peptide libraries, a benzodiazepine library (see e.g., Bunin et al., 1994, Proc. Natl. Acad. Sci. USA 91:4708–4712) can be adapted for use. Peptoid libraries (Simon et al., 1992, Proc. Natl. Acad. Sci. USA 89:9367–9371) can also be used. Another example of a library that can be used, in which the amide functionalities in peptides have been permethylated to generate a chemically transformed combinatorial library, is described by Ostresh et al. (1994, Proc. Natl. Acad. Sci. USA 91:11138–11142).

A specific embodiment of such an in vitro screening assay is described below. The SP-10 promoter green fluorescent protein reporter vector is used to generate transgenic mice from which primary cultures of SP-10-GFP germ cells are established. About 10,000 cells per well are plated in 96-well plates in total volume of 100 μl, using medium appropriate for the cell line. Candidate inhibitors of SP-10 gene expression are added to the cells. The effect of the inhibitors of SP-10 gene activation can be determined by measuring the response of the green fluorescent protein reporter gene driven by the SP-10 promoter. This assay could easily be set up in a high-throughput screening mode for evaluation of compound libraries in a 96-well format that reduce (or increase) green fluorescent protein activity, but which are not cytotoxic. After 6 hr. incubation, 100 μl DMEM medium +2.5% fetal bovine serum (FBS) to 1.25% final serum concentration is added to the cells, which are incubated for a total of 24 hours (18 hours more). At 24 hours, the plates are washed with PBS, blot dried, and frozen at −80° C. The plates are thawed the next day measured in a fluorimeter to determine green fluorescent protein activity.

In a preferred example of an in vivo screening assay, spermatogenic cells derived from transgenic mice can be used transplanted into mice with a normal or other desired phenotype (Brinster et al., 1994, Proc. Natl. Acad. Sci. USA 91:11298–302; Ogawa et al., 1997, Int. J. Dev. Biol. 41:111–12). Such mice can then be used to test the effect of compounds and other various factors on fertility and spermatid development. In addition to the compounds and agents listed above, such mice can be used to assay factors or conditions that can be difficult to test using other methods, such as dietary effects, internal pH, temperature, etc.

Once a compound has been identified that inhibits or enhances SP-10 promoter activity, it may then be tested in an animal-based assay to determine if the compound exhibits the ability to act as a contraceptive or to ameliorate symptoms of a SP-10 mediated disorder, such as infertility.

5.4 Compositions and Methods for Therapeutic use of SP-10 Nucleotides

SP-10 polynucleotides, or transcriptionally active fragments thereof, can be used to treat diseases, conditions, or disorders that can be ameliorated by modifying the level or the expression of SP-10, or a heterologous gene linked to an SP-10 promoter, in a testes-specific manner. Described herein are methods for such therapeutic treatments.

The SP-10 gene promoter region may be used to achieve tissue specific expression in gene therapy protocols. In cases where such cells are tumor cells, the induction of a cytotoxic product by the SP-10 gene promoter region may be used in the form of cancer gene therapy specifically targeted to testicular tumor cells which contain trans acting factors required for SP-10 expression. In this way the SP-10 promoter may serve as a delivery route for a gene therapy approach to testicular cancer. Additionally, antisense, antigene, or aptameric oligonucleotides may be delivered to cells using the presently described expression constructs. Ribozymes or single-stranded RNA can also be expressed in a cell to inhibit the expression of a target gene of interest. The target genes for these antisense or ribozyme molecules should be those encoding gene products that are essential for cell maintenance.

The SP-10 promoter region and transcriptionally active fragments thereof of the present invention may be used for a wide variety of purposes, e.g., to down regulate SP-10 gene expression, or, alternatively, to achieve testis-specific stage-specific expression of heterologous genes.

In one embodiment, for example, the endogenous SP-10 promoter region maybe targeted to specifically down-regulate expression of the SP-10 gene. For example, oligonucleotides complementary to the regulatory region may be designed and delivered to the cells. Such oligonucleotides may anneal to the regulatory sequence and prevent transcription activation. Alternatively, the regulatory sequence or portions thereof may be delivered to cells in saturating concentrations to compete for transcription factor binding. For general reviews of the methods of gene therapy, see Goldspiel et al., 1993, Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIBTECH 11:155–215. Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In another embodiment, a gene therapy method for contraception is provided. SP-10 promoter sequences are used to drive spermatid-specific expression of drugs or toxins and introduced in the testis. The method comprises introducing an SP-10 regulatory sequence operatively associated with a drug or toxin gene into testicular cells.

In yet another embodiment, the invention provides a gene therapy method for treatment of cancer or other proliferative disorder. The SP-10 promoter is used to direct the expression of one or more proteins specifically in testicular tumor cells of a patient. Such proteins may be, for example, tumor suppressor genes, thymidine kinase (used in combination with acyclovir), toxins, or proteins involved in cell killing, such as proteins involved in the apoptosis pathway.

Methods for introducing genes for expression in mammalian cells are well known in the field. Generally, for such gene therapy methods, the nucleic acid is directly administered in vivo into a target cell or a transgenic mouse that expresses SP-10 promoter operably linked to a reporter gene. This can be accomplished by any methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), by direct injection of naked DNA, by use of microparticle bombardment (e.g., a gene gun; Biolistic, Dupont), by coating with lipids or cell-surface receptors or transfecting agents, by encapsulation in liposomes, microparticles, or microcapsules, by administering it in linkage to a peptide which is known to enter the nucleus, or by administering it in linkage to a ligand subject to receptor-mediated endocytosis (see e.g., Wu and Wu, 1987, J. Biol. Chem. 262:4429–4432), which can be used to target cell types specifically expressing the receptors. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992; WO 92/22635 dated Dec. 23, 1992; WO92/20316 dated Nov. 26, 1992; WO93/14188 dated Jul. 22, 1993; WO 93/20221 dated Oct. 14, 1993). Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijlstra et al., 1989, Nature 342:435–438).

The oligonucleotide may comprise at least one modified base moiety which is selected from the group including, but not limited to: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

Endogenous target gene expression can also be reduced by inactivating or "knocking out" the SP-10 regulatory region using targeted homologous recombination (e.g., see Smithies et al., 1985, Nature 317:230–234; Thomas and Capecchi, 1987, Cell 51:503–512; Thompson et al., 1989, Cell 5:313–321; each of which is incorporated by reference herein in its entirety). For example, a mutant, non-functional target gene (or a completely unrelated DNA sequence) flanked by DNA homologous to the promoter region of the SP-10 gene can be used, with or without a selectable marker and/or a negative selectable marker, to transfect cells that express the target gene in vivo. Insertion of the DNA construct, via targeted homologous recombination, results in inactivation of the SP-10 promoter. This approach can be adapted for use in humans provided the recombinant DNA constructs are directly administered or targeted to the required site in vivo using appropriate vectors.

In an alternative embodiment, endogenous target gene expression can be reduced by targeting deoxyribonucleotide sequences complementary to the SP-10 regulatory region to form triple helical structures that prevent transcription of the target gene in target cells in the body. (See generally, Helene, 1991, Anticancer Drug Des., 6(6):569–584; Helene et al., 1992, Ann. N.Y. Acad. Sci., 660:27–36; and Maher, 1992, Bioassays 14(12):807–815).

Nucleic acid molecules to be used in triple helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

In a specific embodiment, single-stranded deoxynucleotides are designed to target the 38 bp element shown highlighted in FIG. 3. Alternatively, the potential sequences that can be targeted for triple helix formation may be increased by creating a so called "switchback" nucleic acid molecule. Switchback molecules are synthesized in an alternating 5'–3', 3'–5' manner, such that they base pair with first one strand of a duplex and then the other, eliminating the necessity for a sizeable stretch of either purines or pyrimidines to be present on one strand of a duplex.

The anti-sense RNA and DNA molecules and triple helix molecules of the invention may be prepared by any method known in the art for the synthesis of nucleic acid molecules. These include techniques for chemically synthesizing oligodeoxyri-bonucleotides well known in the art such as for example solid phase phosphoramidite chemical synthesis. Alternatively, RNA molecules may be generated by in vitro and in vivo transcription of DNA sequences encoding the RNA molecule. Such DNA sequences may be incorporated into a wide variety of vectors which contain suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include, but are not limited to, the addition of flanking sequences of ribo- or deoxy- nucleotides to the 5' and/or 3' ends of the molecule or the use of phosphorothioate or 2' O-methyl rather than phospho-diesterase linkages within the oligodeoxyribonucleotide backbone.

The SP-10 promoter region and transcriptionally active fragments thereof of the present invention can be used to express the SP-10 gene in an altered manner as compared to expression in a normal cell. The SP-10 promoter region and transcriptionally active fragments thereof of the present invention can also be used to achieve tissue specific expression of a target gene. Thus, it is possible to design appropriate therapeutic and diagnostic techniques directed to this regulatory sequence in order to modulate the expression of a target gene. In accordance with the present invention, the term "modulate" encompasses the suppression or augmentation of expression of a target gene and also encompasses the tissue specific suppression or expression of a target gene. When a cell proliferative disorder is associated with under-expression or overexpression of a SP-10 gene product, oligonucleotide based compounds such as those described herein, including antisense oligonucleotides, may be used to modulate expression of the SP-10 gene. For example, this method may be used to restore fertility. In another example, where the associated disorder is cancer, the induction of a cytotoxic gene product SP-10 gene promoter may be used as a cancer therapy. One of skill in the art can determine if a particular therapeutic course of treatment is successful by several methods known to those of skill in the art, including muscle fiber analysis or biopsy.

The assays of the present invention may be first optimized on a small scale (i.e., in test tubes), and then scaled up for high-throughput assays. The screening assays of the present may be performed in vitro, i.e. in test tubes, using purified components or cell lysates. The screening assays of the present invention may also be carried out in intact cells in culture and in animal models. In accordance with the present invention, test compounds which are shown to modulate the activity of SP-10 in vitro, as described herein, will further be assayed in vivo in cultured cells and animal models to determine if the test compound has the similar effects in vivo and to determine the effects of the test compound on meiotic progession, spermatogenisis etc.

In accordance with this embodiment, the systems described below may be formulated into kits. To this end, vectors and cells comprising polynucleotides comprising SP-10 promoter sequences operatively linked to a reporter genes can be packaged in a variety of containers, e.g., vials, tubes, microtiter well plates, bottles, and the like. Other reagents can be included in separate containers and provided with the kit; e.g., positive control samples, negative control samples, buffers, cell culture media, etc.

5.5 Pharmaceutical Preparations and Methods of Administration

The compounds that are determined to modify SP-10 promoter activity or gene product activity can be administered to a patient at therapeutically effective doses to treat or ameliorate a cell proliferative disorder. A therapeutically effective dose refers to that amount of the compound sufficient to result in amelioration of symptoms of such a disorder.

5.5.1 Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

5.5.2 Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

6. EXAMPLE

Delineation of a Promoter Fragment Sufficient for Expression the Acrosomal Protein SP-10 Gene in Transgenic Mice In this Example, the round spermatid-specific expression, genomic cloning, and organization of the mSP-10 gene, as well as delineation of its functional promoter in transgenic mice, is described. This Example demonstrates that the core promoter of mSP-10 gene, including 266 bp of genomic sequence upstream of the germ cell-specific transcriptional start site, and 28 bp of the flanking downstream sequence, contains the necessary promoter elements to mediate round spermatid-specific gene expression.

6.1 Materials and Methods

Screening of a Mouse Genomic Library

The full length mSP-10 cDNA (Reddi et al., 1995, Biol. Reprod. 53:873–881) was used as a probe to screen a mouse liver (C57BL/6N male) genomic library (ML1043j) constructed in EMBL phage vector (Clontech, Palo Alto, Calif.). Plaque hybridization was performed as described (Sambrook et al., 1989, Molecular Cloning: A Laboratory Manual, 2nd ed., Cold Spring Harbor Laboratory Press, NY). Briefly, the library was plated at a density of $10^5$ pfu/150 mm plate using E. coli K802 (Clontech, Palo Alto, Calif.) as the bacterial host strain, and duplicate plaque lifts were transferred to Duralon-UV nylon filter circles (Stratagene, La Jolla, Calif.). Prehybridization of the filters was carried out for two hours at 42° C. in a buffer containing 50% formamide (Sigma Chemicals, St. Louis, Mo.), 6×SSC (1×=0.01 5M sodium citrate, 0. 15M sodium chloride), 5×Denhardt's solution (1×=0.5% each of ficoll, bovine serum albumin, and polyvinyl pyrrolidone), and 1%SDS. The mSP-10 cDNA was $^{32}$P-dCTP labeled using the Prime-a-Gene kit (Promega, Madison, Wis.). Hybridization was performed at 42° C. for 20 hours in the prehybridization buffer consisting of $10^6$cpm/ml of radiolabeled mSP-10 cDNA probe. The filters were washed in a buffer containing 2×SSC, 1%SDS at room temperature for 30 minutes, at 65° C. for one hour, and at 65° C. in 0.2×SSC and 1%SDS for one hour. The dried filters were exposed to autoradiographic film (Kodak, Rochester, N.Y.) at −70° C. Only signals obtained in duplicate were considered positive, and the corresponding plaques were cored out from the plates. For plaque purification, secondary and tertiary screenings were done at a density of $10^2$-$10^3$ pfu/150 mm plate.

mSP-10 Genomic Clones

A total of twenty genomic phage clones which hybridized with the mSP-10 cDNA were plaque purified. The clone λ3, containing the largest insert (14 kb) was further analyzed. Oligonucleotide probes originating from the 5' untranslated region (5'UTR) (5' TCTTCTCAGCTCTTGAGTGTGC-CAC (SEQ ID NO:6), position 11–35, Genbank accession #U31992) and 3' untranslated region (3'UTR) (5' GCTCT-GACTTAGGCAGGTTCACCAC (SEQ ID NO:7), position 871–895, Genbank accession #U31992) of mSP10 cDNA were $\gamma^{32}$P-ATP end-labeled using T4 Kinase (Promega, Madison, Wis.) according to the manufacturer's instructions. The two radiolabeled oligonucleotides probes were used separately to hybridize to the clone λ3 DNA (Sambrook et al., 1989). Both probes hybridized with the clone λ3 DNA indicating that the 14 kb insert contained the entire mSP-10 genomic sequence. Restriction mapping revealed three internal EcoRI sites, splitting the 14 kb insert of clone λ3 into 4.7, 3.8, 3.2 and 2.2 kb fragments which were subcloned separately into Bluescript vector to yield p 1.4, p2.1, p3.4, and p4.1 respectively. The orientation of the genomic sub-fragments was determined based on the hybridization of oligonucleotides derived from mSP-10 cDNA, and DNA sequencing (see below). The 5'UTR oligonucleotide probe (position 11–35, Genbank accession #U31992) hybridized to p4.1, suggesting that the 2.2 kb EcoRI fragment contained the 5' end of the gene. Similar analysis using the 3'UTR sequence of SP-10 cDNA (position 871–895, Genbank accession #U31992) placed the p1.4 insert at the 3' end of the gene. Several probes chosen from the middle portion of the cDNA hybridized to the p1.1 clone. Clones p2.1 and p3.4 did not hybridize with probes derived from mSP-10 cDNA.

DNA Sequencing

Nucleotide base sequences of the bluescript plasmids p4.1, p1.4, p3A., and p2.1 containing the SP-10 genomic DNA were obtained by Sanger's dideoxy chain termination method. Initially, the vector based T3 and T7 primers were used, and subsequently new internal primers were synthesized to facilitate further sequencing. In particular, the regions corresponding to exon-intron junctions and the 5' and 3' untranslated regions were sequenced. The entire intronic regions were not sequenced.

Primer Extension Analysis

A 29 mer primer sequence (5' CCCAGTAAGATTAACTCCTTCATTTTGA) (SEQ ID NO:8) complementary to the 60–88 bp region of SP-10 cDNA (Genbank accession #U31992), which included the ATG site, was used to reverse transcribe mLRNAs from mouse testis and liver. Five hundred ng of testis and liver mLRNAs were annealed to 100 fmols of $\lambda^{32}$P-ATP end-labeled 29 mer primer. First strand cDNA synthesis was performed using the AMV Reverse Transcriptase Primer Extension System (Promega, Madison, Wis.) according to the manufacturer's instructions. Primer extension products were analysed by polyacrylamide gels containing 8% acrylamide, 7M urea in 1×TBE (89 mM Tris, 110 mM boric acid, 2 mM EDTA, pH 8.0). Standard M13 dideoxy chain termination sequencing reaction products were run alongside to provide molecular size markers. The length of the primer extension products reflected the total number of bases between the labeled nucleotide of the primer and the 5' end of the RNA.

Reporter Gene Constructs

Three promoter fragments of mSP-10, whose 5' ends started from −408, −270, or −91 bp and whose 3' position terminated at base pair +28 with reference to the transcription start site; were cloned upstream of GFP cDNA using reporter vector pEGFP1 (Clontech, Palo Alto, Calif.). The −408 to +28 bp, and −91 to +28 bp mSP-10 fragments were PCR amplified from mouse genomic lambda clone 3 using as 5' end primers 5' CCCCTCGAGCCTCCAATCTTAG-GACTAACCTCAG (SEQ ID NO:9) and 5' CCCCTC-GAGAAGAGGAACAACCCATTGTGA (SEQ ID NO:10) (Xho I site in italics), respectively, and a common 3' end primer with the sequence 5' GGGGGATCCTGGCACACT-CAAGAGCTGAGA (SEQ ID NO:11) (BamH I site in italics). Vent DNA polymerase (New England Biolabs Inc., Beverly, Mass.) was used in 25 cycle reactions. The PCR products were cleaved with Xho I and BamH I, and ligated to Xho I+BamH I cleaved pEGFPi vector to yield −408SP10-gfp and −91SP10-gfp constructs which were verified by DNA sequencing. The −408SP10-gfp and −91SP10-gfp plasmids were cleaved with Xho I and Aft II (pEGFP1, bp#1058) to generate the −408 and −91SP10-gfp transgenes, each consisting of a mSP-10 promoter segment, GFP, and SV40 polyadenylation signals. The third, −266SP 10-gfp transgene was derived by cleavage of the −408SP10-gfp clone using Hinc II (at −266 in mSP-10, FIG. 4) and Aft II, which released a 1352 bp fragment. The −408, −266 and −91 transgenes were gel purified prior to injection.

Generation of Transgenic Mice

Transgenic mice were produced by microinjection of transgenes into the male pronuclei of fertilized mouse eggs and transfer of these eggs to psuedopregnant foster mothers using standard procedures (Hogan et al., 1986, Manipulating the Mouse Embryo. Cold Spring Harbor Press, NY). Transgenic mice were generated by the Transgenic Mouse Core Facility (TMCF) at the University of Virginia. Transgenic founder mice were identified by two methods. (1) Tail DNA was subjected to PCR amplification using GFP primers; 5' GTGAGCAAGGGCGAGGAGCTG (SEQ ID NO:12) (nt#100–120, GenBank accession #U 55761) and 5' CTTG-TACAGCTCGTCCATGCCGAG (SEQ ID NO:13) (nt#8 13–790, Genbank accession #U55761) spanning a 713 bp portion of the GFP cDNA. Mouse SP-10 genomic DNA primers (5' CCTCCAATCTTAGGACTAACCTCAG (SEQ ID NO:14) and 5' TGGCACACTCAAGAGCTGAGA (SEQ ID NO:15) were used as a positive internal control. The amplification of 713 bp gfp PCR product identified the founder mice. (2) Transgene integration was confirmed by Southern hybridization (Sambrook et al., 1989, Molecular Cloning: A Laboratory Manual, 2nd ed., Cold Spring Harbor Laboratory Press, NY.). Mouse genomic DNAs were cut with EcoR I, transferred to nylon membrane (Stratagene, La Jolla, Calif.), and probed with radiolabeled GFP cDNA (derived from pEGFP 1). The filters were washed under the same conditions as described under "screening of a mouse genomic library". The founder mice were identified on the basis of positive hybridization band(s) obtained with the gfp probe. The positive founders were mated with C57 B1 partners to obtain an F1 generation for analysis. Adequate numbers of founder transgenic mice were generated for each construct to allow interpretation of the outcome. Two out of three −408SP10-gfp founder lines, and six out of six −266SP10-gfp founder lines expressed GFP in a testis-specific manner. The third −408SP10-gfp founder line did not express GFP in any tissue. Three out of three −91SP10-gfp founder lines also failed to express GFP in any tissue.

GFP Expression in Transgenic Mice:

Six to 8 week old F1 transgenic males were sacrificed according to the guidelines provided by the institution, and tissues were collected in sterile PBS to study the expression of GFP. The testes of transgenic and non-transgenic littermates were decapsulated and observed using a Zeiss Axiovert fluorescence microscope with FITC filters (24). Cell squashes were prepared as follows: 2–3 millimeter pieces of seminiferous tubules were cut and transferred to a glass slide, and a cover slip was then placed on the preparation to obtain a monolayer of cells. The seminiferous tubules expressing GFP appeared bright green when viewed using the FITC optics. Somatic tissues including brain, liver, lung, heart, kidney, muscle, intestine, spleen, seminal vesicle, and prostate from transgenic and nontransgenic mice were also processed and examined for GFP production.

RT-PCR

Poly A+RNAs isolated from testes and several somatic tissues of transgenic animals were reverse transcribed using an RT-PCR kit (Stratagene, La Jolla, Calif.) according to the manufacturer's instructions. The poly A+RNA samples were routinely treated with DNAse and extracted with phenol chloroform prior to use in RT-PCR. PCR was then performed using the GFP-specific primers described above. Production of a 713 bp PCR product indicated the presence of transgene mRNA. PCR using mouse beta-actin primers (5' gtgggccgctctaggcaccaa, and 5' ctctttgatgtcacgcacgatttc) served as an internal control. Appearance of a 500 bp beta actin PCR product indicated the reaction conditions for reverse transcription and PCR were appropriate.

In situ Hybridization

The testes of sexually mature mice were collected in 10% neutral buffered formalin (Sigma Chemicals, St. Louis, Mo.). Processing of tissue samples, and sectioning was carried out as previously described (Stoler, 1990, Clin. Lab. Med. 10:215–236). In situ hybridization was performed using mSP-10 and GFP riboprobes. For the purpose of in vitro synthesis of riboprobes, mSP-10 and GFP cDNAs were cloned into the Bluescript vector (Stratagene, La Jolla, Calif.). The mSP-10 cDNA was excised from pETmSP-10 (Reddi et al., 1995, Biol. Reprod.53:873–881) using EcoR I and BamH I and cloned into the vector to yield pBS-SP1o. The pEGFP1 vector was cut with Kpn I and Not I to release GFP cDNA, which was then ligated to Kpn I+Not I treated pBSII KS- vector to yield pBS-gfp. Radiolabeled sense and antisense mSP-10 and GFP probes were generated from linearized plasmids by incorporating $[^{5\text{-}3}H]$ CTP and $[^{5,6\text{-}3}H]$ UTP (Amersham, Piscataway, N.J.) using Riboprobe Combination System (Promega, Madison, Wis.). The hybridization and wash conditions were as described (Stoler, 1990, Clin. Lab. Med. 10:215–236.).

Detection of GFP in the Developing Testis Male pups born to the −266SP10-gfp mice were sacrificed at daily intervals between days 14 and 35 post partum. The day of birth was considered as day 1. Testes were collected in sterile PBS, the seminiferous tubules were teased and 2–3 mm sections were cut. Cell squashes were prepared as described above and observed using Zeiss Axiovert fluorescence microscope fitted with FITC filter. The spermatogenic cell types were identified according to established criteria (Russel et al., 1990, Histological and Histopathological Evaluation of the Testis, 1st Ed., Cache River Press, Clearwater, Fla.) under phase contrast. Photographs were obtained using a digital camera (Hamamatsu, Bridgewater, N.J.) and Adobe Photoshop (San Jose, Calif.) software.

Database Searches

The mouse SP-10 5' flanking sequence was subjected to a database search to identify putative transcription factor binding sites, using the Tfsites program (Genetics Computer Group, Madison, Wis.).

6.2 Results 6.2.1 Round Spermatid-specific Expression of mSP10

In situ hybridization was performed to localize mSP-10 gene expression during spermatogenesis. In the mouse, the cycle of the seminiferous epithelium has been divided into 12 consecutive stages, each stage characterized by a constant cell association (Russel et al., 1990, Histological and Histopathological Evaluation of the Testis, 1st Ed., Cache River Press, Clearwater, Fla.). In a typical cross-section of mouse testis, seminiferous tubules representing various stages of the cycle are observed (FIG. 8). The mSP-10 IMRNA hybridization signal was restricted to seminiferous tubules at stages I through VII of the cycle; there was no mSP-10 expression at stages VIII through XII. An example of mSP-10 expression in the mouse germinal epithelium is illustrated in FIG. 8. The mSP-10 mRNA hybridization signal was abundant at stage UL, which is characterized by the presence of numerous round spermatids and a single layer of pachytene spermatocytes, but was greatly diminished at stage VII of the cycle (FIG. 8A), in which elongate spermatids (s16) typically line the lumenal surface of the seminiferous epithelium (FIG. 8B). The mSP-10 mRNA expression was seen predominantly over the cytoplasm of the round spermatids at stage III, whereas in all other germ cell types including spermatogonia, spermatocytes, or late spermatids at either stage (FIG. 8A) the hybridization signal was not above the background obtained by probing with the mSP-10 sense riboprobe. The in situ data indicate that mSP-10 mRNA expression is transient and stage-dependent being highly expressed in early round spermatids, coincident with acrosome biogenesis. Expression of the mSP-10 gene thus represents an example of testis-specific transcription activity during the initial phase of spermiogenesis.

6.2.2 Genomic Organization of mSP-10 Gene

A 750 bp mSP-10 cDNA fragment (Reddi et al., 1995, Biol. Reprod. 53:873–881) was used as a probe to screen a mouse liver EMBL genomic library (Clontech, Palo Alto, Calif.); twenty clones reactive with the probe were identified and plaque purified by tertiary screening. One of the genomic clones containing a 14 kb insert hybridized to oligonucleotide probes originating from the 5' as well as the 3'UTR of mSP-10 cDNA, indicating that this insert contained the entire gene (FIG. 1). Subcloning and sequencing of the 14 kb genomic DNA insert showed that the mSP-10 gene consisted of four exons spread over a 5.5 kb region (FIG. 1). Exons 1 through 4 corresponded to nucleotides 1 through 107, 108 through 599, 600 through 719, and 720 through 1067. Nucleotide sequences of these exons were identical to the mouse SP-10 cDNA (Genbank accession #U31992). Introns 1 through 3 were determined to be 0.8, 1.9, and 1.7 kb in length (Table I). The sequences at the exon-intron boundaries of the mSP-10 gene were consistent with the higher eukaryotic splice sequences which aid in the removal of introns. The 5' splice donor and 3' splice acceptor sequences of mSP-10 gene conformed to the consensus eukaryotic splice site sequences AG\gtaag (5' donor) and cag/G (3' acceptor). Similarly, a canonical branch point sequence (consensus YNCURAY) and a poly pyrimidine tract (Kramer et al., 1996, Annu.

Rev. Biochem. 65:367–409) are located at appropriate positions upstream of the 3' splice acceptor site of each intron of the mSP-10 gene (Table 1). It is interesting to note that the introns consistently interrupted the exons of the mSP-10 gene between the first and second bases of a codon. FIG. 1 also shows the exon organization in relation to the protein structure. Each exon encoded a structural part of the SP-10 protein previously characterized in the human and mouse (Wright et al., 1990, Biol. Reprod. 42:693–701; Liu et al., 1992, Biol. Reprod. 46:937–948.). Exon 1 included 59 bp of 5'UTR and the first 17 amino acids of the SP-10 protein which constituted the signal peptide. Exon 2 encoded the 164 amino acid hydrophilic core of the protein. Exons 3 and 4 included the carboxyl terminus of the protein which was shown to be conserved among the mouse, human, baboon and macaque SP-10 cDNAs (Freemerman et al., 1993, Mol. Repr. Dev. 34:140–148).

6.2.3 Transcriptional Start Site of mSP-10

The transcriptional start site of the mSP-10 gene was determined by the primer extension method. A radiolabeled 29-mer oligonucleotide primer complementary to nucleotides −5 to +24 bp relative to the ATG codon (FIG. 4, broken underline) was hybridized to mRNAs from mouse testis and liver, and the first strand synthesis was carried out in the presence of AMV reverse transcriptase. The reaction products were analyzed on a denaturing sequencing gel alongside a size marker (FIG. 1). One major extension product (arrow) of 82 bases was obtained with testis (T) but not with liver (L) mRNA (FIG. 1). Based on the length of the primer extension product, the adenosine residue located 58 nucleotides upstream of the ATG was determined to be the transcription initiation site (FIG. 4, +1). None of the mSP-10 cDNA clones sequenced to date contained additional sequence upstream of the +1 site determined by this method, indicating that mSP-10 transcription is initiated from a single site.

6.2.4 5' Flanking Sequence of SP-10 Gene

The core promoter of the mouse SP-10 gene lacks a canonical TATA box in the −25 bp position but contains a pyrimidine rich initiator (Inr) sequence in the −2 to +5 bp position, encompassing the transcription start site (FIG. 4). The mSP-10 Inr sequence (5' TCA$^{+1}$GT$^{+3}$TT) conforms to the consensus eukaryotic mr sequence 5' YYANTYY (Y is a pyrimidine, N=any nucleotide), in which the +1 and +3 positions are invariably occupied by A and T respectively (Gregory et al., 1993, Mol. Cell. Biol. 13:3841–3849). In eukaryotic promoters which lack a TATA box, the Inr element has been shown to be sufficient for accurate transcription initiation (Smale & Baltimore, 1989, Cell 57:103–113). The human SP-10 promoter also lacks a TATA box and like the mouse gene, contains a consensus Inr element surrounding the transcriptional start point (Wright et al., 1993, Biol. Reprod. 49:316–325, FIG. 4). A comparison of the mouse SP-10 promoter sequence with the previously published 5' flanking sequence of the human SP-10 gene (Wright et al., 1993, Biol. Reprod. 49:316–325, Genbank accession #S65606s1) revealed that the −408 to +58 bp region of the mouse gene shared 67% identity and 80% similarity with the −459 to +67 bp human gene sequence (FIG.4). In contrast, regions further upstream in both gene promoters shared less than 50% homology.

Several identical cis sequences were shared by the two promoters (highlighted regions in FIG. 4), some of which constituted recognition sites for known transcription factors. A CAT box, typically located close to the transcription start site in the eukaryotic promoters, is found at −404 bp in the mouse and at −455 bp in the human SP-10 promoter. A consensus GATA-1 binding sequence was located at −242 in the mouse (5' CTATCT), and at −280 (5' AGATAT) in the human. The transcription factor GATA-1, which plays a critical role in the differentiation of the hematopoietic system, has also been shown to be highly expressed in the testis (Ito et al., 1993, Nature, 362:466–468). A consensus Ets-1 binding site, 5' CAGGATGT, was located at −99 bp in the mouse. The human SP-10 promoter also contained an Ets-1 site, 5' CAGGCTAC at −110 bp, but this deviated from the consensus at the two positions underlined. A 5'-CCCC sequence, which has a high affinity for the ETF transcription factor, is conserved at −169 and −200 in mouse and human respectively. The ETF factor preferentially activates transcription from TATA less promoters (Kageyama et al., 1989, J. Biol. Chem. 380:159–162).

One notable feature of the proximal SP-10 promoter region is the conservation of three palindrome sequences (FIG. 4). Palindromes P1, P2, and P3 positioned at −47 (5'TTCTAGAA), −105 (5' CCTGaaCAGG) (SEQ ID NO:16), and −141 bp 5' CACTAGTG in the mouse, are conserved at −49, −116 and −157 bp positions respectively in the human (shaded boxes in FIG. 4). It is well known that palindrome sequences constitute the half sites recognized by transcription factors, but no recognition sites for known transcription factors were found within the SP-10 palindromes. A 16 bp T-rich region was conserved at −202 and −231 positions in the mouse and human respectively. There were no GC-rich elements or Sp1 binding sites in the SP-10 promoter.

The mouse and human SP-10 promoters contain a sequence similar to the consensus cyclic AMP response element (CRE, 5'TGACGTCA) at −74 (5'TGAGGACA) and −76 (5'TGAAGAAA) positions respectively. The cognate transcription factor CREMπ (cyclic AMP response element modulator tau) was previously shown to be essential for the transcription of a number of testis-specific genes which contain the CRE sequence in their proximal promoter. However, it is important to emphasize that CREM-deficient mice continued to produce SP-10 mRNA in the testis[2] indicating that CREM is probably not involved in SP-10 transcription. In addition to the shared promoter elements, there were some transcription factor binding sites unique to the mouse promoter including an E-box site (5' CATGTG) at −221, HNF-5 (5'TG'1T1'GT) at −198 and AP1 site (5'TGA'TTCA) at −27 positions respectively (FIG. 4). The presence of an E-box is particularly noteworthy in view of the recently identified germ cell-specific, E-box binding transcription factor, FIG-(Factor In the Germline) alpha (Liang et al., 1997, Development 124:4939–4947).

6.2.5 Generation of Transgenic Mice

Figure 5A:
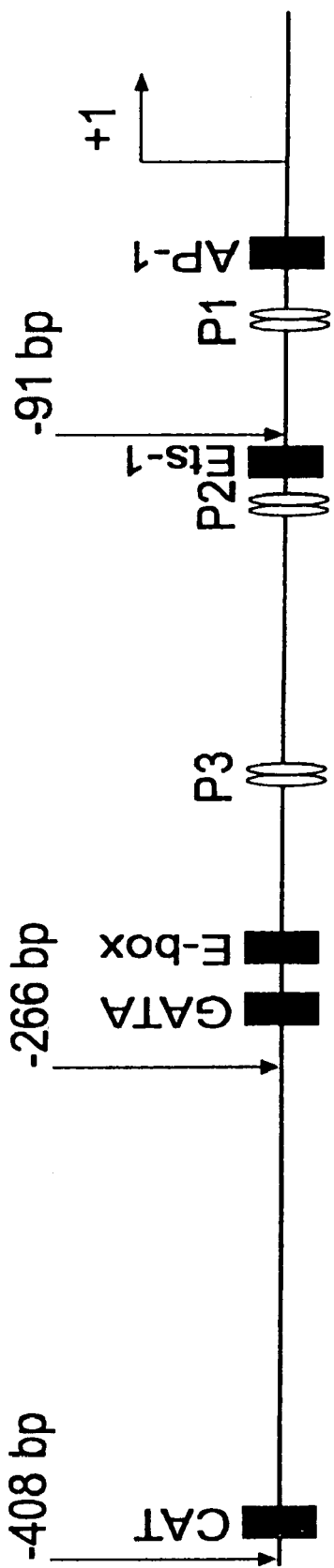
Figure 5B:
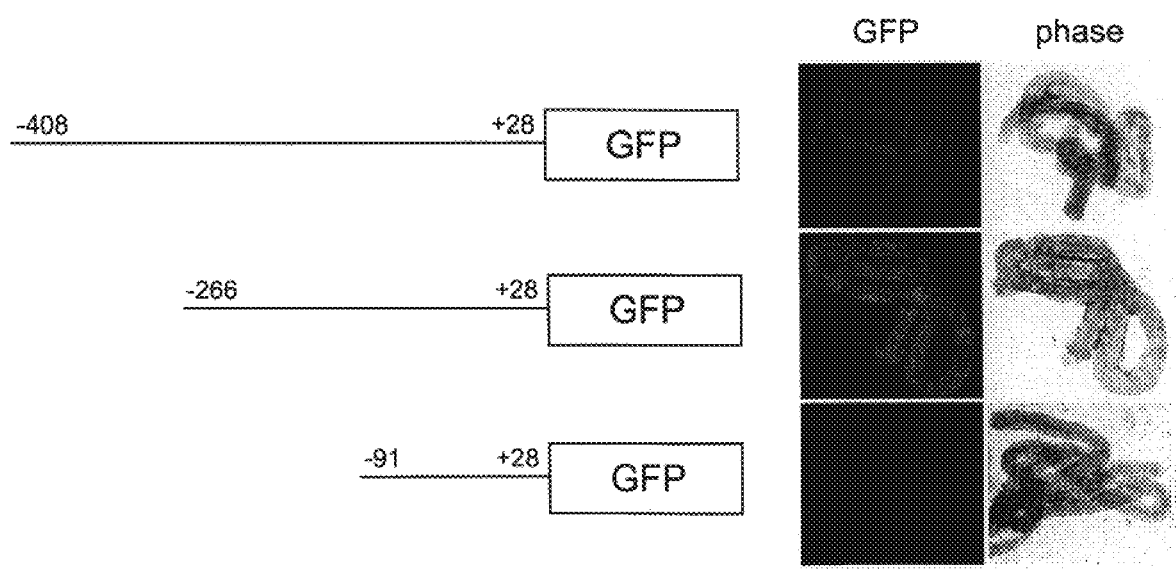

The high degree of similarity between mouse and human sequences observed in the SP-10 proximal promoter region (FIG. 4) may indicate conservation of functionally important cis-acting elements responsible for testis-specific transcription. The putative regulatory elements within the conserved −408 to +28 bp mSP-10 promoter region are schematically represented in FIG. 5A. To identify the minimal mSP-10 promoter region required to drive testis-specific gene expression in transgenic mice, three separate reporter gene constructs were made. A mSP-10 promoter containing the: 1) −408 to +28 bp; 2) −266 to +28 bp; or 3) −91 to +28 bp fragment was linked to GFP cDNA (FIG. 5B). Transgenic founder mice were identified by PCR amplification of the GFP sequence, and the integration of the transgene in each line was confirmed by Southern hybridization (see materials and methods). Three founders containing the −408 to +28 bp fragment, six founders containing the −266 to +28 bp fragment and three founders containing the −91 to +28 bp fragment were identified.

6.2.6 Testis-Specific Expression of GFP in Transgenic Mice

Six to 8 week old F1 transgenic males were sacrificed and tissues were examined for reporter gene expression. Since the fluorescence emanating from GFP expressing cells could be visualized using a microscope fitted with the FITC filter set, freshly isolated tissue samples were directly examined to detect reporter gene activity. Tissues obtained from non-transgenic littermates served as negative controls. Fluorescence microscopy demonstrated GFP expression in the seminiferous tubules from mice containing the −408SP10-gfp, and −266SP10-gfp constructs, but not the −91SP10-gfp construct (FIG. 5B). Cell squashes prepared from multiple somatic tissues including, brain, liver, lung, heart, kidney, muscle, intestine, spleen, seminal vesicle, and prostate of all three transgenic lines were negative for GFP expression (data not shown), indicating that the transgene expression in −408SP10-gfp and −266SP10-gfp mice was testis-specific. The −91SP10-gfp mice failed to express GFP in any tissue.

Figure 5C:
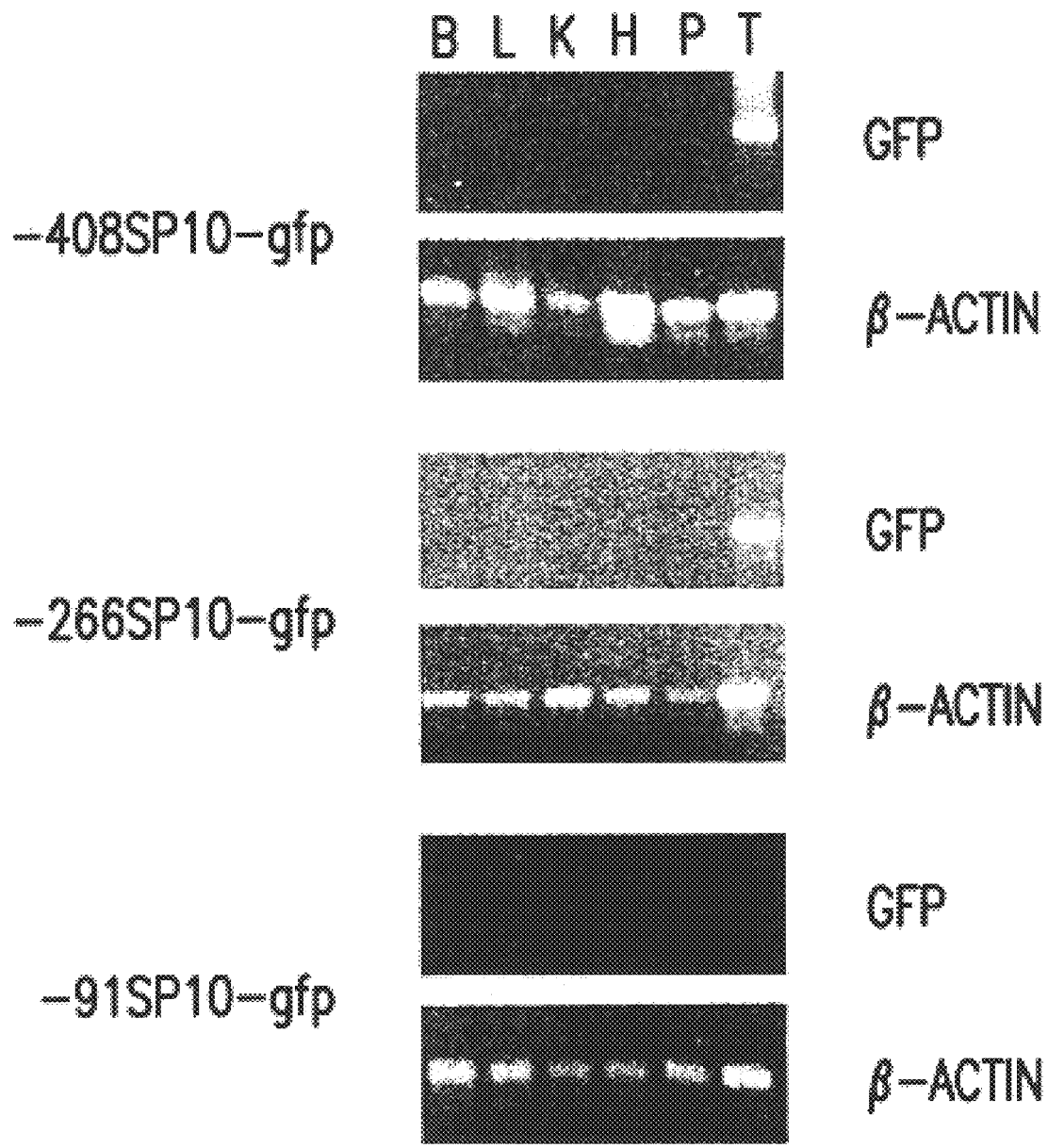

The testis-specificity of GFP expression was confirmed using RT-PCR. Messenger RNA obtained from various tissues of transgenic mice was reverse transcribed and subjected to PCR amplification using GFP- and beta actin-specific oligonucleotide primers (see methods). The 713 bp PCR product indicative of the presence of GFP mRNA was detected in the testes of the −408SP10-gfp, and −266SP10-gfp mice, but not the −91SP10-gfp mice (FIG. 5C). On the other hand, no GFP RT-PCR product was obtained from the somatic tissues including brain, liver, kidney, heart, or prostate. All the tissues examined amplified the 500 bp product corresponding to beta actin control (FIG. 5C). These results indicated that the −408 to +28 bp, or −266 to +28 bp mSP-10 promoter fragments contain the cis-elements required to drive testis-specific expression of a reporter gene in transgenic mice. In contrast, the −91 to +28 bp mSP-10 region by itself was insufficient to activate gene expression in any tissue. It is interesting to note that recognition motifs for GATA-1, bHLH proteins, HNF-5, Ets-1, as well as two conserved palindrome sequences P3 and P2 were located within the −266 to −92 bp region of the mSP-10 promoter (FIG. 5A).

Of three −408SP10gfp founder mice, two expressed GFP in a testis-specific manner, but the third showed no GFP expression in any tissue, possibly owing to a position effect. Six out of six −266SP10gfp founder lines expressed GFP in the testis alone, whereas all the three −91SP10gfp lines revealed no trace of transgene expression in any tissue.

6.2.7 Spatial and Temporal Pattern of Transgene Expression

In situ hybridization was performed on serial cross-sections of the testis of a −408SP10-gfp transgenic mouse using SP-10 and GFP riboprobes to compare the spatio-30 temporal distribution of transgene mRNA in the seminiferous epithelium with that of the endogenous SP-10. As expected, the SP-10 antisense probe hybridized with only a subset of tubules in the cross- section (FIG. 6A) reflecting the stage-specificity observed previously. More important, the GFP antisense probe produced an identical hybridization pattern in adjacent cross sections (FIG. 6B). Thus, the GFP mRNA expression was confined to the same stages of the seminiferous epithelium at which the endogenous mSP-10 gene was also expressed. Similarly, the lack of transgene expression was coincident with the absence of SP-10 expression (compare panels A and B in FIG. 6). These results indicate that the −408 to +28 bp mSP-10 promoter fragment contains the necessary transcription regulation signals responsible for both temporal and testis-specific gene expression in transgenic mice.

6.2.8 The −266 to +28 bp mSP-10 Promoter is Sufficient to Direct Round Spermatid-Specific Gene Expression In Vivo Since germ cells of the mouse undergo synchronous differentiation during the first spermatogenic cycle in the developing testis, it was possible to precisely determine the germ cell type in which the transgene expression was initiated by assaying GFP expression in the developing testis of the transgenic mice. It is known that type A and type B spermatogonia appear by day 8, early and late pachytene spermatocytes by days 14 and 18 respectively, and haploid spermatids between days 18–20 post partum in the developing testis (Bellve et al., 1977, J. Cell. Biol. 74:68–85). Therefore, seminiferous tubules of−266SP10-gfp transgenic mice ranging from 14 to 35 days in age at daily intervals were examined to detect the first appearance of GFP fluorescence. Non-transgenic littermates served as negative controls (data not shown). The seminiferous tubules of 18 and 21 day old transgenic mice are shown in FIG. 7 to illustrate the transgene expression pattern. No GFP expression was seen in the pachytene spenatocytes of the day 18 testis (FIG. 7, Ps, GFP). GFP was first detected over round spermatids, which made their appearance in the day 21 testis (FIG. 7, Rs, GFP), indicating that the transgene expression was initiated postmeiotically. Spermatocytes at day 21 remained negative for GFP expression, indicating that the SP-10 promoter is quiescent in germ cells undergoing meiosis (FIG. 7, Ps, GFP). The data from this developmental series clearly indicate that the −266 to +28 bp mSP-10 promoter region activated gene expression during the early haploid phase of spermatogenesis in vivo.

To identify cis-acting elements within the SP-10 promoter which interact with transcription factors, electromobility shift assays (EMSAs) and southwestern analysis were performed. A 45 kDa nuclear protein from testis exhibited strong binding to a 38 bp double stranded oligonucleotide (38-mer) shown in shaded highlighting in FIG. 3, located at the −185 bp position of the SP-10 promoter. The interaction of the 38-mer with the 45 kDa protein appears to be testis-specific; no reactivity was found in the 45 kDa region when nuclear extracts from liver, lung, kidney, brain, or spleen were tested. It was interesting to note, however, that the 38-mer bound with a faint band at 45 kDa in the brain extract.

Next, the binding site for the 45 kDa testis nuclear protein was determined by introducing mutations in various positions within the 38-mer. A 5' ACACAC element is essential for interaction with the 45 kDa binding activity. There are two 5' ACACAC repeats within the 38-mer, separated by a six-base pair spacer. Data obtained from EMSA and SWA indicate that the kDa nuclear protein occupies the 5' ACACAC site as a monomer, and forms a dimer via protein-protein interaction when both sites are occupied. The principal finding is that a 5' ACACAC ci-element present at −185 bp position in the SP-10 promoter, interacts with a 45 kDa testis-nuclear protein.

6.3 Discussion

Promoter analysis of testis-specific genes, which are temporally expressed during spermatogenesis, and the identification of the cognate transcription factors will likely lead to an understanding of the regulatory pathways governing the complex male germ cell differentiation program. Herein the identification of a minimal SP-10 promoter capable of directing round spermatid-specific gene expression in transgenic mice is described.

In-situ hybridization showed that the SP-10 gene exhibited a germ cell type—and stage-dependent pattern of temporal gene expression. Transcription of the mSP-10 gene was abundant in postmeiotic round spermatids at stage III, and the mRNA signal rapidly declined in spermatids at stage VII. One interpretation of this data is that the transcription factor(s) responsible for initiating SP-10 gene expression appears de novo and/or attains a functional form in the round spermatids.

Primer extension identified one major transcription initiation site for the mSP-10 gene. The sequence surrounding this transcriptional start point, TCAGTTT, was consistent with that of the consensus Inr sequence first identified in the promoter of the gene for terminal deoxytransferase (TdT) by Smale and Baltimore (Smale & Baltimore, 1989, Cell 57:103–113). The mSP-10 gene promoter lacks a consensus TATA box in the −25 region. However, unlike other testis-specific genes lacking TATA boxes, such as acrosin and Ldhc-4 for which multiple transcription start points were observed (Nayernia et al., 1994, J. Biol. Chem. 51:32181–32186; Cooker et al., 1993, Biol. Reprod. 48:1309–1319), the SP-10 gene exhibited only one major mRNA start site embedded within the Inr sequence. This indicates that core promoter elements other than TATA may play a role in accurate initiation of SP-10 transcription. It is interesting to note that the transcription start site of human, baboon, and macaque SP10 genes also mapped within a consensus Inr sequence (Freemerman et al., 1993, Mol. Repr. Dev. 34:140–148; Wright et al., 1993, Biol. Reprod. 49:316–325). In higher eukaryotes, Inr was shown to be a core promoter element capable of recruiting the preinitiation complex and determining the transcription start site in the absence of a TATA box (Gregory et al., 1993, Mol. Cell. Biol. 13:3841–3849). The conserved SP-10 Inr, which is similar to the Inr elements of TdT or adenovirus major late promoter gene (Smale & Baltimore, 1989, Cell 57:103–113), may serve to assemble the basal transcription complex, while further upstream promoter elements may be responsible for mediating testis-specific transcription of SP-10 mRNA.

The observation that a 408 bp sequence upstream of the transcription start site of the mouse SP-10 gene shared 80% similarity with a corresponding region in the human SP-10 promoter prompted the prediction that functionally important promoter elements may be conserved within this region. Transgenic mice demonstrated that a −408 to +28 bp mSP-10 promoter fragment contains the necessary promoter elements to drive testis-specific expression of a reporter gene. In these mice, the promoter activity of the −408 to +28 bp fragment mimicked that of the endogenous mSP-10 gene, in that the transgene expression was confined to the same stages of the cycle of the seminiferous epithelium as SP-10 MRNA. When the SP-10 promoter was truncated from the 5' end to contain a −266 to +28 bp fragment, the resulting transgenic mice also expressed GFP mRNA in the testis alone. The developmental appearance of the GFP protein in 21 day old, but not the 18 day old, transgenic mouse testis was consistent with promoter activity of the −266 to +28 bp fragment in postmeiotic round spermatids. Upon further truncation, however, the SP-10 promoter lost its activity, as transgenic mice bearing the −91 to +28 bp SP-10 promoter failed to express the transgene in any tissue.

Taken together, the experiments on transgenic mice indicated that the cis-acting elements which play a critical role in early round spermatid gene expression reside within the −266 to +28 bp SP-10 promoter region. It is interesting to note that sites for GATA-1, E-box binding protein(−220), HNF-5 (−196 bp), and Ets-1 (−99 bp) are located within the −266 to −91 bp region of the SP-10 promoter, as are two conserved palindrome sequences at −106 and −141 positions. When compared to the promoters of other testis-specific genes expressed in the round spermatids, including acrosin (Nayemia et al., 1994, J. Biol. Chem. 51:32181–32186), the −408 to +28 bp SP-10 promoter did not show any significant homology. The cis-acting elements shown to be indispensable for the testis-specific expression of reporter genes in vivo, such as the CTCCAG repeats within the GCP1 sequence of proenkephalin gene (Liu et al., 1996, J. Biol. Chem. 272:5056–5062), the 31 bp palindrome of the lactate dehydrogenase c (Li et al., 1998, J. Biol. Chem. 273:31191–31194), or the TE element of histone H1t gene promoter (vanWert et al., 1998, Biol. Reprod. 59:704–710), were not shared by the novel mSP-10 promoter identified in this study. This result, however, is consistent with the fact that the transcription of the mouse acrosin, proenkephalin, Ldhc-4 and H1t genes is initiated during the meiotic phase in spermatocytes whereas SP10 gene expression is initiated postmeiotically in round spermatids. Therefore the cis regulatory elements involved in SP-10 gene transcription may be expected to differ.

Recent reports have demonstrated key roles for the testis-specific transcription factors A-myb and CREMτ during spermatocyte and spermatid differentiation, respectively. It appears that CREMτ does not control early spermatid gene expression as evidenced by the formation of step 1 spermatids in CREM knockout mice, as well as the continued presence of mRNAs for both proacrosin (Nantel et al., 1996, Nature 389:159–162) and mSP-10 in these mice. Although several testis-specific transcripts whose expression is initiated in the round spermatids were characterized, no information on their promoter analyses is available (Penttila et al., 1995, Biol. Reprod. 53:499–5 10). Identification of promoter regions of additional testis-specific genes which drive round spermatid-specific gene expression in vivo, as was done in the present study, will provide clues to a common regulatory mechanism required for early spermiogenesis. One interesting observation that has emerged from the promoter analysis of the mSP-10 gene is that a relatively short proximal promoter piece (294 bp) was sufficient to drive testis-specific gene expression in vivo. Short proximal promoter regions of other testis-specific genes, including protamine 1 (119 bp), t-ACE (91 bp) proenkephalin (119 bp), Pdha-2 (187 bp), and Ldhc-4 (100 bp), were also shown to be adequate for germ line-specific activity in transgenic mice (Zambrowicz et al., 1993, Proc. Natl. Acad. Sci. U. S. A. 90:5071–5075; Howard. et al., 1993, Mol. Cell. Biol., 13:18–27; Liu et al., 1996, J. Biol. Chem. 272:5056–5062; lannello et al., 1997, Mol. Cell. Biol. 17:612–619; Li et al., 1998, J. Biol. Chem. 273:31191–31194) indicating that core promoter structure might be critical for testis-specific gene activation.

This is the first reported identification of a testis-specific gene promoter which activates round spermatid-specific gene expression. The −266 to +28 bp SP-10 promoter region can be dissected further to determine cis-elements which interact with nuclear proteins from testis. The SP-10 gene promoter identified here thus may provide a useful tool to identify germ cell type-specific transcription factors, and other compounds that modulate such transcription.

7. EXAMPLE

Generation of Transgenic Mice Expressing Green Fluorescent Protein Under the Control of SP-10 Regulatory Sequences Identification of the stage of spernatogenesis, and the germ cell type in which the transgenic transcription has been initiated, is critical to the analysis of testis-specific promoters. The choice of the reporter gene and the assays required to detect reporter gene activity, play an important role in determining the spatial and temporal gene expression pattern imparted by the promoter fragment. Green fluorescent protein (GFP), derived from the jellyfish Aequorea victoria (Prasher et al., 1992, Gene 111:229), is particularly useful as a reporter molecule in the testis. Since GFP emits bright green fluorescence when excited by blue light, live spermatogenic cells expressing GFP under the control of a testis-specific promoter can be identified by fluorescence microscopy. When coupled with a transillumination-assisted microdissection technique (Parvinen & Vauha-Perttula, 1972, Anat. Rec. 174:435), which permits the isolation of stages of spermatogenesis from freshly dissected seminiferous tubules, the developmental stage- and cell type-specific onset of promoter activity can be accurately determined. Visualization of GFP does not require incubation with exogenous substrates or cofactors. This contrasts to other reporter genes previously expressed in the testis such as the bacterial β-galactosidase or the mammalian growth hormone genes, which require fixation of the tissues, sectioning, and cytochemical or immunological staining for detection (Peschon et al., 1987, Proc. Natl. Acad. Sci. U.S.A. 84: 5316; Stewart et al., 1988, Mol. Cell. Biol. 8, 17:48; Howard et al., 1993, Mol. Cell. Biol. 13:18). Recently, using the GFP reporter system, the promoter of a testis-specific gene SP-10 (Kurth et al., 1991, Biol. Reprod. 44:814; Kurth et al., 1993, Anat. Rec. 236:619; Reddi et al., 1995, Biol. Reprod. 53:873) in transgenic mice has been dissected, and a −420 to +28 base pair (bp) promoter region identified to be sufficient for round spermatid-specific gene expression (see Section 6, above). In this Section is described examples of GFP expression in the testes of transgenic mice. As described in detail below, transgenic mice expressing GFP in mouse testis have been generated. This GFP is under the control of the SP-10 promoter. The GFP is turned on in spermatids. In mature sperm, the GFP persists in the cytoplasmic droplet. Thus, the transgenic mice of the present invention described below provide for the analysis and manipulation of testes-specific expression in vivo.

Stage- and cell type-specific expression of GFP under the control of SP-10 promoter Stages of the seminiferous epithelium from 6 to 8 week old SP-10-GFP mice as well as non-transgenic littermates were identified and isolated using the transillumination-assisted microdissection technique. A slide containing a segment from desired stage of the cycle was placed under an inverted Nikon Diaphot-TMD microscope equipped with a GFP filter and an electronically controlled Lambda 10–2 shutter (Sutter Instrument Co., Novato, Calif.). The cells were analyzed using a Nikon planapochromat 60×(N.A. 1.4) objective and the images of GFP-SP-10 expressing cells and control cells were captured using a cooled CCD SenSys camera (Photometrics, Tucson, Ariz.) and processed with Metamorph image analysis software (Universal Imaging Corp., West Chester, Pa.). Images of monolayered germ cells from each stage of the cycle were captured and analysed. To limit the fading of the GFP signal, exposure times were kept as low as possible (0.2 to 0.8 sec).

Photomicrographs representing stages XI–XII, I, V, IX from SP-10-GFP mice are shown in FIG. 8B. The stages were identified based on the morphology of the developing acrosomes and the nuclei of the spermatids. At stage I, two steps of spermatids may be identified; early post-meiotic step 1, and elongated step 3 spermatids. The step 1 spermatids have round nuclei with prominent nucleoli, whereas the step 13 spermatids have prominent hook shaped nuclei (Stage I, s13 in FIG. 8B). The step 5 spermatids at stage V are characterized by the developing acrosomic system spreading over the nuclear envelope. At stage IX, the only haploid cells are step 9 spermatids with elongated nuclei. Stage XII is characterized by the presence of meiotic divisions. Identification of fluorescent germ cells at various stages of spermatogenesis indicated that the expression of GFP under the control of SP-10 promoter starts only after meiotic divisions. No GFP signal was observed during meiosis: preleptotene, leptotene, zygotene, pachytene and meiotically dividing spermatocytes from SP-10-GFP transgenic mice did not fluoresce green. The GFP signal was first observed in early post-meiotic step 1 spermatids where a dim green fluorescence was present diffusely throughout the cells (FIG. 8B, Rs). This is consistent with the expression pattern of the endogenous SP-10 gene. It has been previously observed that mRNA and protein of SP-10 appear post-meiotically, in the early round spermatids (Herr, 1990, Biol. Reprod. 42:377–382). The GFP signal, which was more intense in the later steps of spermatid development, persisted in all postmeiotic germ cell types from step 1 to step 16 spermatids, probably due to the long half life of the protein. Analysis of the stages of non-transgenic littermates (control mice) showed no fluorescent cells at any stages of the cycle.

GFP reporter gene constructs

The SP-10-GFP mice, in which GFP is placed under the control of the SP-10 promoter, were analysed following this procedure. Bright green fluorescence was observed only in the testicular cells. All somatic tissues obtained from the SF-10-GFP mouse as well as all tissues from the control mouse were negative for GFP, indicating that the SP-10 promoter fragment used in this study directed testis-specific gene expression. The seminiferous tubules from these mice appeared bright green in color whereas those from the control mice did not fluoresce (FIG. 8A). Thus the GFP reporter construct allowed rapid visualization of signal in living tissues, without the need for fixing, sectioning, cytochemical or immunological staining of the tissue. As described below, the spatio-temporal pattern of transgene expression during spermatogenesis was next characterized.

GFP detection in isolated stages of mouse spermatogenesis

The development and differentiation of spermatozoa occurs inside seminiferous tubules in three main phases. First, mitotic proliferation of sperinatogonia produces mature spermatogonia (type B) that divide to form preleptotene spermnatocytes. This initiates meiosis. After meiotic DNA synthesis is completed, the spermatocytes initiate a long pachytene phase during which many meiosis specific events occur, including pairing of the homologous chromosomes (synapsis) and formation of the synaptonemal complex. Two successive cell divisions at the end of melosis give rise to haploid spermatids, that subsequently undergo many morphological changes to form mature spermatozoa during the differentiation phase called speriniogenesis.

In the seminiferous epithelium, different germ cell populations are regularly associated with each other at specific phases of development (FIG. 9). These cell associations, also called the stages of the seminiferous epithelium, follow each other in a wave-like fashion along the seminiferous epithelium. One stage progresses to the next in a cyclic fashion at regular time intervals, without any longitudinal movement along the axis of the tubule, creating what has been termed the cycle of the seminiferous epithelium (Leblond & Clermont, 1952, Ann. N.Y. Acad. Sci. 55:548). In mouse, the cycle of the seminiferous epithelium is divided into 12 stages that are classically identified according to the morphology of the developing acrosomes and the nucleus of early spermatids.

Figure 10A:
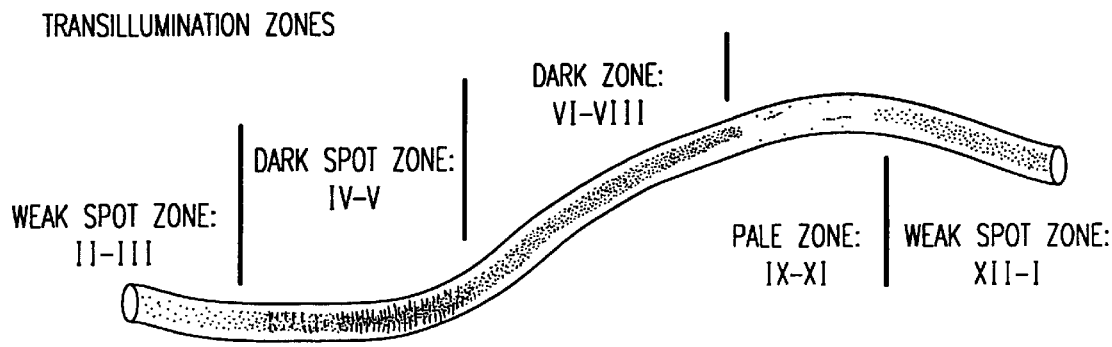
Figure 10B:
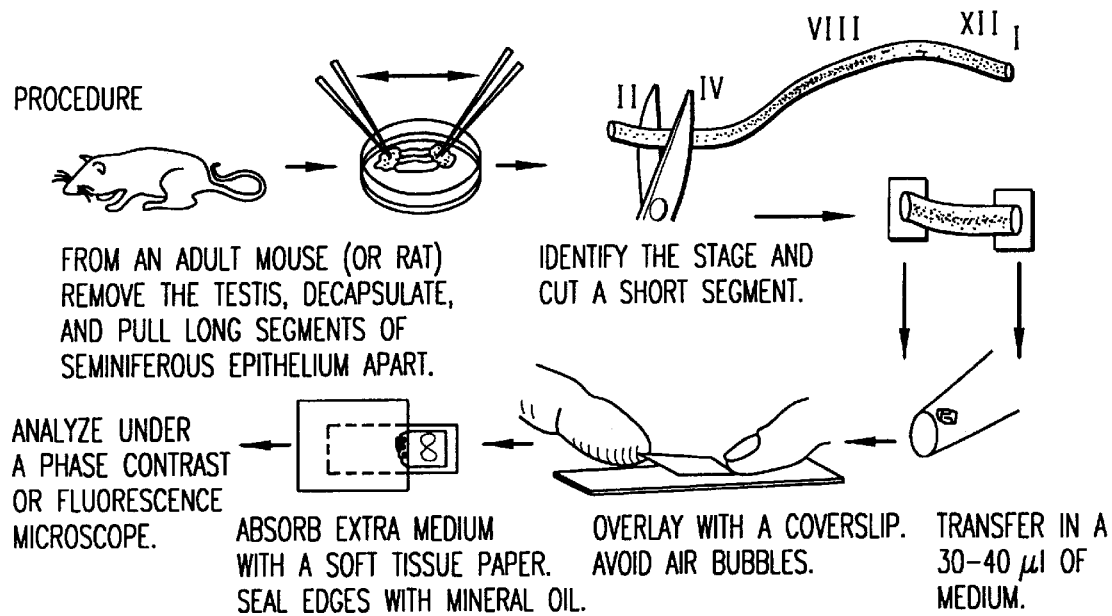

Transillumination-assisted microdissection method for identification and isolation of stages of mouse spermatogenesis In the early 1970s, a transillumination-assisted microdissection method enabling a fast and accurate identification and isolation of mouse and rat stages was developed and later improved (Parvinen & Vauha-Perttula, 1972, Anat. Rec. 174:435; Parvinen et al., 1993, in *Methods in Toxicology*, Chapin & Heindel, eds., Vol 3, part A, 142, Academic Press, New York). Recently, this technique has been successfully applied in a variety of morphological, biochemical, and toxicological studies on mouse and rat spermatogenesis (Parvinen & Hecht, 1981, Histochemistry 71:567; Penttilä et al., 1995, Biol. Reprod. 53:499; Kalijo et al., 1998, Dev. Biol. 195:29; Yan et al., 1997, Mol. Cell. Endocrinol. 132:137; Penttilä et al., 1995, Mol. Cell. Endocrinol. 113:175; Sjöblom &. Lähdetie, 1996, Oncogene 12:2499). The method is based on the specific light absorption patterns of the mouse and rat seminiferous tubules caused by the cyclic changes in the chromatin condensation of haploid germ cells and in the localization of elongating spermatids within the seminiferous epithelium (Parvinen & Ruokonen, 1982, J. Androl. 3: 211). In brief, an isolated segment of mouse seminiferous tubule contains four main light absorption zones (FIG. 10A). The "pale" zone consisting of stages IX–XI allows passage of most of the light. The "weak spot" zone containing stages XII–III is more light absorbent because of the formation of bundles of elongating spermatids at steps 12–14. As the Formation of spermatid bundles inreases and the association of step 15 spermatids with the Sertoli cells deepens, the "weak spot" zone turns into a "dark spot" zone (stages IV–V). The "dark" zone (stages VI–VII) is characterized by the release of the bundle arrangement of the step 15 spermatids and localization of the step 16spermatids at the lumenal edge of the seminiferous epithelium. When spermiation occurs at the end of stage VIII of the seminiferous cycle the dark zone stops and the pale zone reappears.

The invention described and claimed herein is not to be limited in scope by the specific embodiments herein disclosed since these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. Throughout this application various references are cited, the contents of each of which is hereby incorporated by reference into the present application in its entirety.

What is claimed is:

1. An isolated DNA segment consisting of the nucleotide sequence depicted in FIG. 3 (SEQ ID NO:1).

2. An isolated DNA segment consisting of the nucleotide sequence from −266 to +28 of the nucleotide sequence depicted in FIG. 3 (nucleotide residue 143 to 146 of SEQ ID NO:1).

3. A vector comprising the DNA segment of claim 1 or 2 operably linked with a nucleotide sequence that encodes a reporter protein.

4. A vector comprising the DNA segment of claim 1 or 2.

5. A recombinant cell transformed with the vector of claim 3.

6. The vector of claim 3, wherein the reporter protein is selected from the group consisting of green fluorescent protein, luciferase, and β-galactosidase.

* * * * *

UNITED STATES PATENT AND TRADEMARK OFFICE
CERTIFICATE OF CORRECTION

PATENT NO. : 6,355,480 B1
DATED : March 12, 2002
INVENTOR(S) : Reddi et al.

It is certified that error appears in the above-identified patent and that said Letters Patent is hereby corrected as shown below:

<u>Column 45,</u>
Line 27, "146" should be -- 436 --.

Signed and Sealed this

Tenth Day of September, 2002

Attest:

Attesting Officer

JAMES E. ROGAN
*Director of the United States Patent and Trademark Office*

SEQUENCE LISTING

<160> NUMBER OF SEQ ID NOS: 16

<210> SEQ ID NO 1
<211> LENGTH: 436
<212> TYPE: DNA
<213> ORGANISM: Mus musculus

<400> SEQUENCE: 1

```
cctccaatct taggactaac ctcagtttga agccaaaacc actcagctaa tctcagcaaa      60
gattagtctt ccagagtgca aaccagagcc atgaaacact cagtcaaaca gaaagtaacc     120
aggtcaccac acttcactgt tgaccctctg caaagaagtg ctatctttta aactttcact     180 aaagaacat gtgtgattct ggtaacattt tttgtttgtt tttgaagcta ccctaacac      240 actattctac acacagaaaa tgctcttcac tagtggcatt gcatgggttg cagggccagc     300
ctgcctgaac aggatgtaag aggaacaacc cattgtgagg acacatagat tgtttctcaa     360
gttctagaat tcccagaggc tctgattcaa cactgggagc gtttgctcag tttcttctca     420
gctcttgagt gtgcca                                                     436
```

<210> SEQ ID NO 2
<211> LENGTH: 500
<212> TYPE: DNA
<213> ORGANISM: Mus musculus

<400> SEQUENCE: 2

```
gcctccaatc ttaggactaa cctcagtttg aagccaaaac cactcagcta atctcagcaa      60
agattagtct tccagagtgc aaaccagagc catgaaaacac tcagtcaaac agaaagtaac    120
caggtcacca cacttcactg ttgaccctct gcaaagaagt gctatctttt aaactttcac    180
taaaagaaca tgtgtgattc tggtaacatt ttttgtttgt ttttgaagct accccctaaca    240 cactattcta cacacagaaa atgctcttca ctagtggcat tgcatgggtt gcagggccag     300
cctgcctgaa caggatgtaa gaggaacaac ccattgtgag gacacataga ttgtttctca     360
agttctagaa ttcccagagg ctctgattca cactgggag cgtttgctca gtttcttctc      420
agctcttgag tgtgccacat tagagatctt tatttaccta aatcaaaatg aaggagttaa     480
tcttaatggg tctttatctg                                                 500
```

<210> SEQ ID NO 3
<211> LENGTH: 559
<212> TYPE: DNA
<213> ORGANISM: Homo sapiens

<400> SEQUENCE: 3

```
ccctccaatc ctgtataaac ccaatctgaa gccaaatcca gccagcattc aggtgataaa      60
gtcaacagag gtcaaccttc cagggtacag atcagagcc agaaaggctg atttagaaag     120
ccaaacagaa aacaatcaac aattacatct cattgtcaaa aacactttta aaagacagta    180
gatatctttt aaactttatt acaaaaaata tgtgcttttt ggtaatactt ttttttttt     240
tttaaagata gggcagatag ccccaacaca ctaccctgca cacagaaaat aatcattggt    300
cttcactagt gaaataagca gtgggttgct aagggccaac ttgcctgaac aggctacaca    360
agaacctcag agcccaaccc attgtgaaga acatgggtt acttctgagg ttctagaatt     420
cccagaagct ctgcttcagc actggaagct tttgctcgca gtttgcttca tagctctgtg    480
aagaagctgt ggcccacact ggggtcccct cttttcctaa atccagatga acaggtttct    540
cttgctaatg agtctttat                                                 559
```

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4

```
atggtgagca agggcgagga gctg                                            24
```

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5

```
gagccgtacc tgctcgacat gttc                                            24
```

<210> SEQ ID NO 6
<211> LENGTH: 25
<212> TYPE: DNA
<213> ORGANISM: Artificial Sequence
<220> FEATURE:
<223> OTHER INFORMATION: oligonucleotide

<400> SEQUENCE: 6

```
tcttctcagc tcttgagtgt gccac                                           25
```

<210> SEQ ID NO 7
<211> LENGTH: 25
<212> TYPE: DNA
<213> ORGANISM: Artificial Sequence
<220> FEATURE:
<223> OTHER INFORMATION: oligonucleotide

<400> SEQUENCE: 7

```
gctctgactt aggcaggttc accac                                           25
```

<210> SEQ ID NO 8
<211> LENGTH: 29
<212> TYPE: DNA
<213> ORGANISM: Artificial Sequence
<220> FEATURE:
<223> OTHER INFORMATION: Primer

```
<400> SEQUENCE: 8
acccagtaag attaactcct tcattttga                                  29

<210> SEQ ID NO 9
<211> LENGTH: 34
<212> TYPE: DNA
<213> ORGANISM: Artificial Sequence
<220> FEATURE:
<223> OTHER INFORMATION: Primer

<400> SEQUENCE: 9
cccctcgagc ctccaatctt aggactaacc tcag                            34

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10
cccctcgaga agaggaacaa cccattgtga                                 30

<210> SEQ ID NO 11
<211> LENGTH: 30
<212> TYPE: DNA
<213> ORGANISM: Artificial Sequence
<220> FEATURE:
<223> OTHER INFORMATION: Primer

<400> SEQUENCE: 11
gggggatcct ggcacactca agagctgaga                                 30

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
gtgagcaagg gcgaggagct g                                          21

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
cttgtacagc tcgtccatgc cgag                                       24

<210> SEQ ID NO 14
<211> LENGTH: 25
<212> TYPE: DNA
<213> ORGANISM: Artificial Sequence
<220> FEATURE:
<223> OTHER INFORMATION: Primer

<400> SEQUENCE: 14
cctccaatct taggactaac ctcag                                      25

<210> SEQ ID NO 15
<211> LENGTH: 21
```

```
<212> TYPE: DNA
<213> ORGANISM: Artificial Sequence
<220> FEATURE:
<223> OTHER INFORMATION: Primer

<400> SEQUENCE: 15
tggcacactc aagagctgag a                                              21

<210> SEQ ID NO 16
<211> LENGTH: 10
<212> TYPE: DNA
<213> ORGANISM: Artificial Sequence
<220> FEATURE:
<223> OTHER INFORMATION: Primer

<400> SEQUENCE: 16
cctgaacagg                                                           10
```